US012648720B2

(12) United States Patent
Presley et al.

(10) Patent No.: US 12,648,720 B2
(45) Date of Patent: Jun. 9, 2026

(54) HIGHLY POROUS, BIORESORBABLE ELECTROSPUN SENSORS FOR OPTICAL DETECTION OF TISSUE OXYGENATION

(71) Applicant: Government of the United States, as represented by the Secretary of the Air Force, Wright-Patterson AFB, OH (US)

(72) Inventors: Kayla F. Presley, Beavercreek, OH (US); Tod A. Grusenmeyer, Kettering, OH (US); Matthew J. Dalton, Bellbrook, OH (US); Jack T. Ly, Kettering, OH (US); Krysta Waldrop, Chandler, AZ (US); Francisco J. Chaparro, Phoenix, AZ (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 497 days.

(21) Appl. No.: 18/142,843

(22) Filed: May 3, 2023

(65) Prior Publication Data

US 2023/0355144 A1 Nov. 9, 2023

Related U.S. Application Data

(60) Provisional application No. 63/339,621, filed on May 9, 2022.

(51) Int. Cl.
*A61B 5/1455* (2006.01)
*A61B 5/1459* (2006.01)
(Continued)

(52) U.S. Cl.
CPC ........ *A61B 5/14552* (2013.01); *A61B 5/1459* (2013.01); *D01D 5/0038* (2013.01);
(Continued)

(58) Field of Classification Search
CPC ... A61B 5/14552; A61B 5/1459; A61B 5/684; D01D 5/0038; D01D 5/0069;
(Continued)

(56) References Cited

U.S. PATENT DOCUMENTS

| | | | | |
|---|---|---|---|---|
| 6,402,037 | B1 * | 6/2002 | Prasad | A61K 49/0084 235/487 |
| 10,117,613 | B2 | 11/2018 | Wisniewski et al. | |

(Continued)

OTHER PUBLICATIONS

Presley, K.F.; Reinsch, B.M.; Cybyk, D.B.; Ly, J.T., Schweller; R.M., Dalton, M.J.; Lannutti, J.J.; Grusenmeyer, T.A.; Oxygen sensing performance of biodegradable electrospun nanofibers: Influence of fiber composition and core-shell geometry. Sensors and Actuators B: Chemical, 2020, 329, 129191, 1-11.

(Continued)

*Primary Examiner* — Edwyn Labaze
(74) *Attorney, Agent, or Firm* — AFMCLO/JAZ; Richard M. Mescher

(57) ABSTRACT

The present invention relates to highly porous, bioresorbable electrospun sensors for optical detection of tissue oxygenation and processes of making and using same. Multiple sensor compositions are described that are focused on different applications/oxygen ranges. Such sensors alleviate the risk of leaving the sensor implanted in a subject, typically have as good or better oxygen sensing capabilities and comparable performance life span as non-degradable sensors and unlike sensors made from general bioresorbable materials maintain a desired porosity as they degrade. Thus, such sensors may remain integrated in a subject's body while they degrade and maintain the ability to sense oxygen for their performance life span.

25 Claims, 24 Drawing Sheets
(7 of 24 Drawing Sheet(s) Filed in Color)

(51) Int. Cl.
*D01D 5/00* (2006.01)
*D01F 1/04* (2006.01)
*D01F 6/62* (2006.01)
*D01F 6/84* (2006.01)

(52) U.S. Cl.
CPC ......... *D01D 5/0069* (2013.01); *D01D 5/0092* (2013.01); *D01F 1/04* (2013.01); *D01F 6/625* (2013.01); *D01F 6/84* (2013.01); *A61B 2562/0233* (2013.01); *A61B 2562/12* (2013.01); *D10B 2331/041* (2013.01); *D10B 2509/00* (2013.01)

(58) Field of Classification Search
CPC .......... D01D 5/0092; D01F 1/04; D01F 6/25; D01F 6/84
USPC ......................................... 235/439, 435, 375
See application file for complete search history.

(56) References Cited

U.S. PATENT DOCUMENTS 10,631,766 B2 4/2020 Sia et al.
10,874,337 B2 12/2020 Gamsey et al.
2013/0046227 A1* 2/2013 Hyde ................. G01N 15/0205 602/41
2016/0041135 A1* 2/2016 Lannutti ............ G01N 21/6428 436/136
2018/0088112 A1* 3/2018 Fan ...................... C12Q 1/6804
2021/0093239 A1 4/2021 Gamsey et al.
2025/0098994 A1* 3/2025 Kaplan ................ G01N 21/643

OTHER PUBLICATIONS

Cybyk, D.B.; Reinsch, B.M.; Presley, K.F.; Schweller, R.M.; Tedeschi, A.; Burns, T.; Chaparro, F.J.; Ly, J.T.; Dalton, M.J.; Lozano, M; Grusenmeyer, T.A.; Biodegradable oxygen biosensors via electrospinning. Med Devices Sens. 2020; 4:e10149. https://doi.org/10.1002/mds3.10149.

Nichols, S.P.; Balaconis, M.K.; Gant, R.M.; Au-Yeung, K.Y.; Wisniewski, N.A.; Long-term in vivo oxygen sensors for peripheral artery disease monitoring. Adv Exp Med Biol. 2018; 1072: 351-356. doi:10.1007/978-3-319-91287-5_56.

Chien, J.S.; Mohammed, M.; Eldik, H.; Ibrahim, M.M.; Martinez, J.; Nichols, S.P.; Wisniewski, N.; Klitzman, B.; Injectable phosphorescence-based oxygen biosensors identify post ischemic reactive hyperoxia. Scientific reports, 2017, 7:8255, 1-10.

Ameer, J.M.; Pr, A.K.; Kasoju, N.; Strategies to tune electrospun scaffold porosity for effective cell response in tissue engineering. J. Funct. Biomater. 2019, 10, 30, 1-21.

Jun. 30, 2020 UES Purchase Order for Electrospinning Services.

May 28, 2021 UES Purchase Order for Electrospinning Services.

Dec. 15, 2021 UES Purchase Order for Electrospinning Services.

Jan. 4, 2023, Presentation by Tod A. Grusenmeyer in Miramar Beach, FL. USA.

Mar. 15, 2022 UES Purchase Order for Electrospinning Services.

* cited by examiner

HIGHLY POROUS, BIORESORBABLE ELECTROSPUN SENSORS FOR OPTICAL DETECTION OF TISSUE OXYGENATION

CROSS-REFERENCE TO RELATED APPLICATION

The present application claims priority to U.S. Provisional Application Ser. No. 63/339,621 filed May 9, 2022, the contents of such provisional application hereby being incorporated by reference in its entry.

RIGHTS OF THE GOVERNMENT

The invention described herein may be manufactured and used by or for the Government of the United States for all governmental purposes without the payment of any royalty.

FIELD OF THE INVENTION

The present invention relates to highly porous, bioresorbable electrospun sensors for optical detection of tissue oxygenation and processes of making and using same.

BACKGROUND OF THE INVENTION

Tissue oxygenation sensors are of interest to provide data about the tissue oxygen level of patients for various medical applications and the tissue oxygen level of pilots during extreme flight conditions. They could also provide useful information about the tissue oxygen level of animals during medical research studies. Such sensors are particularly useful for early indication of hypoxia versus pulse oximetry and provide indication for hyperoxia which pulse oximetry does not. There is potential to provide information on human performance during field operations and to provide physiological information during battlefield trauma and enroute care, specifically related to hypovolemic or hemorrhagic shock, fluid resuscitation, and indication of sepsis, among others. Unfortunately, current tissue oxygenation sensors must be implanted in a subject's body, have a finite performance life span, and can only be removed from a subject's body by an invasive medical procedure that typically carries more risk than leaving the sensor implanted in a subject.

What is needed is a tissue oxygenation sensor that alleviates the risk of leaving the sensor implanted in a subject yet has similar to or better oxygen sensing capabilities and performance life span compared to current sensors. While implants that are bioresorbable may alleviate the risk of leaving the sensor implanted in a subject, such sensors could have performance and life span drawbacks. Applicants recognized that one such issue was that bioresorbable materials, as they degrade, can lose their porosity in a manner that could compromise the tissue integration of these materials in a subject's body. Thus, the ability to sense oxygen declines. Another issue to developing a successful bioresorbable sensor is the need to maintain oxygen sensing capabilities and interpretability despite the dynamic environment of the chromophore as the matrix degrades over time. For developing a successful sensor, it is also important to consider that compositions that exhibit high oxygen sensitivity are ideal for detecting hypoxia, while compositions with moderate oxygen sensitivity exhibit an improved dynamic range and could be better suited for monitoring physoxia and/or hyperoxia. Therefore, multiple sensor compositions could offer utility for a broader range of applications.

In view of the foregoing, Applicants are disclosing herein highly porous, bioresorbable electrospun sensors for optical detection of tissue oxygenation and processes of making and using same. Multiple sensor compositions are described that are focused on different applications/oxygen ranges. Such sensors alleviate the risk of leaving the sensor implanted in a subject, typically have as good or better oxygen sensing capabilities and a comparable performance life span as non-degradable sensors and unlike sensors made from general bioresorbable materials maintain a desired porosity as they degrade. Thus, such sensors may remain integrated in a subject's body while they degrade and maintain the ability to sense oxygen for their performance life span.

SUMMARY OF THE INVENTION

The present invention relates to highly porous, bioresorbable electrospun sensors for optical detection of tissue oxygenation and processes of making and using same. Multiple sensor compositions are described that are focused on different applications/oxygen ranges. Such sensors alleviate the risk of leaving the sensor implanted in a subject, typically have as good or better oxygen sensing capabilities and comparable performance life span as non-degradable sensors and unlike sensors made from general bioresorbable materials maintain a desired porosity as they degrade. Thus, such sensors may remain integrated in a subject's body and maintain the ability to sense oxygen.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
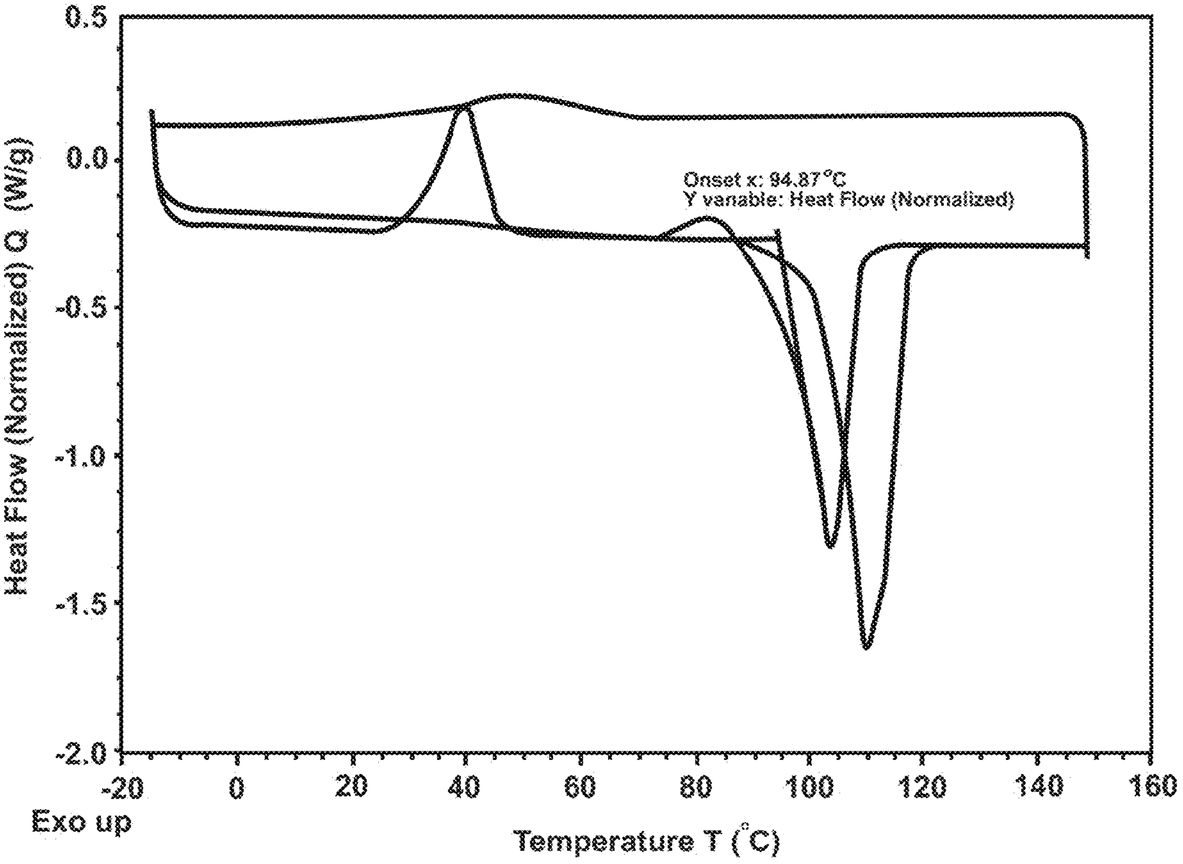
FIG. 1 is the differential scanning calorimetry curves of the poly(p-dioxanone) (PDO) homopolymer.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

DETAILED DESCRIPTION OF THE INVENTION

Sensor and Sensor System

For purposes of this specification, headings are not considered paragraphs. The individual number of each paragraph above and below this paragraph can be determined by reference to this paragraph. In this paragraph, Applicants disclose a sensor comprising a chromophore and a polymer matrix, said chromophore being uniformly dispersed within said polymer matrix, said sensor having a pore length of at least 20 μm or from about 20 μm to about 100 μm, preferably said sensor has a pore length of from about 20 μm to about 50 μm, more preferably said sensor has a pore length of from about 20 μm to about 40 μm, said chromophore being present in mass ratio of chromophore to polymer of from about 1:2000 to about 1:100, preferably said chromophore being present in mass ratio of chromophore to polymer of from about 1:1000 to about 1:100, more preferably said chromophore being present in mass ratio of chromophore to polymer of from about 1:1000 to about 1:125, said chromophore when in said polymer matrix having a deaerated phosphorescence lifetime in 37° C. phosphate-buffered saline of at least 50 μs or from about 50 μs to about 3 ms, preferably said lifetime is from about 90 μs to about 1 ms, more preferably said lifetime is from about 90 μs to about 500 μs, said chromophore when in said polymer matrix exhibiting a red-most absorption maxima and emission maximum of from about 600 nm to about 1300 nm, preferably said red-most absorption maxima and emission maximum are from about 600 nm to about 1000 nm, said chromophore when in said polymer matrix having a difference between the red-most absorption maxima and the emission maximum that is greater than or equal to 50 nm, preferably said difference between the red-most absorption maxima and the emission maximum is from about 100 nm to about 300 nm, preferably said chromophore is selected from the group consisting of Pd (II) and Pt (II) benzoporphyrins and mixtures thereof, more preferably said chromophore is either Pd (II) tetramethacrylated benzoporphyrin, Pt (II) tetramethacrylated benzoporphyrin, Pd (II) meso-tetraphenyl tetrabenzoporphyrin, Pt (II) meso-tetraphenyl tetrabenzoporphyrin and mixtures, more preferably said chromophore is Pd (II) tetramethacrylated benzoporphyrin and said polymer matrix comprising one or more copolymers and/or homopolymers, preferably said one or more copolymers are selected from the group consisting of biocompatible and bioresorbable polyesters, preferably said copolymer is poly(ε-caprolactone-co-p-dioxanone), more preferably said copolymer is a random copolymer, and mixtures thereof and said homopolymers are selected from the group consisting of biocompatible and bioresorbable polyesters, preferably poly(p-dioxanone), poly(ε-caprolactone), and mixtures thereof; said copolymers having each independently a weight-average molecular weight of at least 75,000 Da or said copolymers having each independently a weight-average molecular weight of from about 75,000 Da to about 500,000 Da, preferably said copolymers having each independently a weight-average molecular weight of from about 75,000 Da to about 350,000 Da, more preferably said copolymers having each independently a weight-average molecular weight of from about 115,000 Da to about 350,000 Da; said homopolymers having each independently a weight-average molecular weight of at least 75,000 Da or said homopolymers having each independently a weight-average molecular weight of from about 75,000 Da to about 500,000 Da, preferably said homopolymers having each independently a weight-average molecular weight of from about 75,000 Da to about 350,000 Da, more preferably said homopolymers having each independently a weight-average molecular weight of from about 115,000 Da to about 350,000 Da and/or said homopolymers having each independently an inherent viscosity of at least 1.0 dL/g or said homopolymers each independently having an inherent viscosity from about 1.0 dL/g to about 5.0 dL/g, preferably said homopolymers each independently having an inherent viscosity of from about 1.0 dL/g to about 3.0 dL/g, more preferably said homopolymers each independently having an inherent viscosity of from about 1.5 dL/g to about 3.0 dL/g. In one aspect, said polymer matrix does not comprise silk fibroin. In another aspect, said polymer matrix comprises, based on the total matrix weight, less than 45%, less than 30%, less than 20%, less than 10%, less than 5% or even less than 1% silk fibroin. In one aspect, said polymer matrix does not comprise any natural polymers thus such polymer matrix contains only synthetic polymers. In one aspect, said polymer of said matrix comprises, based on the total polymer weight, a 100% synthetic, biocompatible and bioresorbable polymer.

Applicants disclose the sensor of the previous paragraph wherein said sensor has a fiber diameter of at least 1 μm or from about 1 μm to about 10 μm, preferably said sensor has a fiber diameter of from about 1 μm to about 7 μm, more preferably said sensor has a fiber diameter of from about 1 μm to about 5 μm.

Applicants disclose the sensor of the previous two paragraphs wherein said sensor has a melting point of about 38° C. or higher, preferably said sensor has a melting point of about 40° C. or higher.

Applicants disclose the sensor of the previous three paragraphs wherein said sensor has a rolled cylindrical or rectangular prism geometry.

Applicants disclose the sensor of the previous four paragraphs wherein said sensor has:

a.) a Stern-Volmer quenching constant of from about $1.11\times10^4$ $M^{-1}$ to about $1.00\times10^6 M^{-1}$, preferably said sensor has a Stern-Volmer quenching constant of from about $1.11\times10^4$ $M^{-1}$ to about $2.00\times10^5$ $M^{-1}$, more preferably said sensor has a Stern-Volmer quenching constant of from about $1.43\times10^4$ $M^{-1}$ to about $2.00\times10^5$ $M^{-1}$, most preferably said sensor has a Stern-Volmer quenching constant of from about $2.22\times10^4$ $M^{-1}$ to about $1.43\times10^5$ $M^{-1}$; and/or b.) a dissolved oxygen concentration at which the phosphorescence lifetime of the sensor is quenched to 50% of its deaerated phosphorescence lifetime of from about 1 μM to about 90 μM, preferably said sensor has a dissolved oxygen concentration at which the phosphorescence lifetime of the sensor is quenched to 50% of its deaerated phosphorescence lifetime of from about 5 μM to about 90 μM, more preferably said sensor has a dissolved oxygen concentration at which the phosphorescence lifetime of the sensor is quenched to 50% of its deaerated phosphorescence lifetime of from about 5 μM to about 70 μM, most preferably said sensor has a dissolved oxygen concentration at which the phosphorescence lifetime of the sensor is quenched to 50% of its deaerated phosphorescence lifetime of from about 7 μM to about 45 μM. The Stern-Volmer quenching constant of the sensor is a measure of the sensor's oxygen sensitivity. The dissolved oxygen concentration at which the phosphorescence lifetime of the sensor is quenched to 50% of its deaerated phosphorescence lifetime is typically the inverse of the sensor's Stern-Volmer quenching constant if the sensor exhibits a linear Stern-Volmer plot. This parameter gives an indication of the dissolved oxygen regime for which the oxygen sensor composition is most suitable.

Applicants disclose a sensor system comprising a sensor according to any of the previous five paragraphs and a patch reader, in one aspect said patch reader is a wired or an unwired patch reader that contains a photodetector capable of recording phosphorescence decays of the sensor composition in terms of voltage versus time, preferably said photodetector has a resolution of at least 5 μs, said patch reader comprising a stray excitation light blocking filter covering the photodetector, preferably said stray excitation light blocking filter is a bandpass filter that is centered around the maximum emission wavelength of the sensor, preferably said patch reader comprises a temperature sensor, preferably said temperature sensor records temperature versus time, said patch reader comprises one or more light-emitting diodes having a peak wavelength that at least in part overlaps with a red-most absorption peak of a sensor composition, preferably said light-emitting diodes are intensity-adjustable and have a peak wavelength of from about 600 nm to about 700 nm, and more preferably said patch reader comprises four or more said light-emitting diodes that surround said photodetector. These sensor compositions could be monitored with a wired Beacon system from Profusa, Inc. of Emeryville, California USA or using a wireless patch reader that is a component of Profusa, Inc.'s Wireless Lumee® Oxygen Platform. Suitable patch readers may also be obtained through BaySpec, Inc. or NextFlex of San Jose, California USA.

Process of Making a Sensor

Applicants disclose a process of making a sensor, said process comprising:

a.) electrospinning a solution comprising a solvent, polymer and chromophore to form a sensor scaffold; said solution, comprising, based on total solution weight, of from about 3% to about 20% polymer, preferably said solution comprising of from about 3% to about 15% polymer based on total solution weight, more preferably said solution comprising of from about 5% to about 15% polymer based on total solution weight, said chromophore being present in mass ratio of chromophore to polymer of from about 1:2000 to about 1:100, preferably said chromophore being present in mass ratio of chromophore to polymer of from about 1:1000 to about 1:100, more preferably said chromophore being present in mass ratio of chromophore to polymer of 1:1000 to about 1:125, and said solvent being selected from the group of 1,1,1,3,3,3-hexafluoro-2-propanol, dichloromethane, and mixtures thereof; said electrospinning process having one or more syringes containing said solution, each said syringe being attached to an electrospinning needle, each electrospinning needle independently having an electrospinning needle gauge of from about 14 gauge to 24 gauge, preferably each electrospinning needle independently having an electrospinning needle gauge of from about 16 gauge to about 24 gauge, more preferably each electrospinning needle independently having an electrospinning needle gauge of from about 18 gauge to about 22 gauge, each said needle being translated or being stationary, preferably each electrospinning needle is translated, if each said needle is translated, each electrospinning needle independently having an electrospinning needle translation speed of from about 1 mm/s to about 50 mm/s, preferably each electrospinning needle independently having an electrospinning needle translation speed of from about 5 mm/s to about 30 mm/s, more preferably each electrospinning needle independently having an electrospinning needle translation speed of from about 8 mm/s to about 20 mm/s, each electrospinning needle independently having a flow rate of solution comprising a polymer and chromophore of from about 0.5 mL/hr to about 15 mL/hr, each electrospinning needle independently preferably having a flow rate of solution comprising a polymer and chromophore of from about 1 mL/hr to about 8 mL/hr, more preferably each electrospinning needle independently having a flow rate of solution comprising a polymer and chromophore of from about 1 mL/hr to about 6 mL/hr, each electrospinning needle independently having a voltage applied to said electrospinning needle of from about +5 kV to about +28 kV, preferably each electrospinning needle independently having a voltage applied to said electrospinning needle of from about +6 kV to about +15 kV, more preferably each electrospinning needle independently having a voltage applied to said electrospinning needle) of from about +8 kV to about +12 kV, and one or more electrospinning collectors, each said electrospinning collector independently having a voltage applied to said electrospinning collector of from about −0.2 kV to about −10 kV, preferably each said electrospinning collector independently having a voltage applied to said electrospinning collector of from about −0.2 kV to about −6.0 kV, more preferably each said electrospinning collector independently having a voltage applied to said electrospinning collector of from about −0.2 kV to about −4.0 kV, each said electrospinning collector independently having an electrospinning collector motion linear velocity of from about 50 cm/s to about 600 cm/s, preferably each said electrospinning collector independently having an electrospinning collector motion linear velocity of from about 100 cm/s to about 500 cm/s, more preferably each said electrospinning collector independently having an electrospinning collector motion linear velocity of from about 100 cm/s to about 300 cm/s, said process having a distance between electrospinning needle(s) and electrospinning collector(s) of from 12 cm to about 30 cm, preferably said process having a distance between electrospinning needle(s) and electrospinning collector(s) of from about 14 cm to about 22 cm, more preferably said process having a distance between electrospinning needle(s) and electrospinning collector(s) of from about 18 cm to about 22 cm, said process having a controlled electrospinning exposure temperature of from about 20° C. to about 40° C., preferably said process having a controlled electrospinning exposure temperature of from about 20° C. to about 30° C., more preferably said process having a controlled electrospinning exposure temperature of from about 22° C. to about 26° C., and said process having a controlled electrospinning exposure relative humidity of from about 0% relative humidity to about 50% relative humidity, preferably said process having a controlled electrospinning exposure relative humidity of from about 20% relative humidity to about 50% relative humidity, more preferably said process having a controlled electrospinning exposure relative humidity of from about 35% relative humidity to about 45% relative humidity; preferably said each electrospinning needle is translated and said process employs one electrospinning collector; and b.) processing said sensor scaffold into a sensor by a process comprising rolling and/or cutting said scaffold. Said sensor that is made by this process can be the sensor of the previous six paragraphs.

Method of Monitoring Tissue Oxygenation

Applicants disclose a method of monitoring tissue oxygenation comprising:

a.) stimulating a sensor that is implanted in an animal or human with light having a peak wavelength of from about 600 nm to about 700 nm to cause the emission of light, said light having an emission maximum wavelength of from about 750 nm to about 900 nm, preferably said sensor being a sensor according to any of the previous paragraphs of the section of this specification titled “Sensor and Sensor System”;

b.) fitting the intensity of the emitted light versus time with an exponential function, preferably said exponential function is selected from a monoexponential decay function $I=I_{bkgd}+A\exp(-t/\tau)$, where I is a signal intensity of a chromophore, $I_{bkgd}$ is a background signal intensity of an environment of said chromophore, A is the pre-exponential factor of said monoexponential decay function, t is a time elapsed during a lifetime measurement, and $\tau$ is the phosphorescence lifetime of said chromophore; or a biexponential decay function $I=I_{bkgd}+A_1\exp(-t/\tau_1)+A_2\exp(-t/\tau_2)$, where I is the signal intensity of a chromophore, $I_{bkgd}$ is the background signal intensity of an environment of said chromophore, t is time elapsed during a lifetime measurement, $A_1$ is a first pre-exponential factor of said biexponential decay function, $\tau_1$ is a first phosphorescence lifetime of said chromophore, $A_2$ is a second pre-exponential factor of said biexponential decay function, and $\tau_2$ is a second phosphorescence lifetime of said chromophore;

c.) obtaining a phosphorescence lifetime from said fit; in the case that a biexponential decay function was used, preferably the obtained lifetime is the amplitude average phosphorescence lifetime ($\tau_m=(A_{1\tau1}+A_{2\tau2})/(A_1+A_2)$), where $\tau_m$ is the amplitude average phosphorescence lifetime of said chromophore, $A_1$ is a first pre-exponential factor of said biexponential decay function, $\tau_1$ is a first phosphorescence lifetime of said chromophore, $A_2$ is a second pre-exponential factor of said biexponential decay function, and $\tau_2$ is a second phosphorescence lifetime of said chromophore d.) optionally monitoring said phosphorescence lifetime versus time and/or comparing said phosphorescence lifetime to a calibration, preferably said calibration is performed using the Stern-Volmer equation ($\tau_0/\tau=1+K_{SV}[O_2]$), where $\tau_0$ is the deaerated phosphorescence lifetime of said chromophore, $\tau$ is the phosphorescence lifetime of said chromophore at a dissolved oxygen concentration, $[O_2]$ is a dissolved oxygen concentration, and $K_{SV}$ is the Stern-Volmer quenching constant and $\tau_0$ and $K_{SV}$ are obtained from the in vitro characterization of the composition in 37° C. PBS as described according to this specification’s Test Method 1.

Applicants disclose a method of monitoring tissue oxygenation according to the previous paragraph comprising monitoring said phosphorescence lifetime versus time and/or comparing said phosphorescence lifetime to a calibration, preferably said calibration is performed using the Stern-Volmer equation ($\tau_0/\tau=1+K_{SV}[O_2]$), where $\tau_0$ is the deaerated phosphorescence lifetime of said chromophore, $\tau$ is the phosphorescence lifetime of said chromophore at a dissolved oxygen concentration, $[O_2]$ is a dissolved oxygen concentration, and $K_{SV}$ is the Stern-Volmer quenching constant and $\tau_0$ and $K_{SV}$ are obtained from the in vitro characterization of the composition in 37° C. PBS as described according to this specification’s Test Method 1

Test Methods

Test Method 1 In Vitro Oxygen Sensing Properties of Sensors Test Method. The characterization of polymeric optical tissue oxygenation sensors in a relevant in vitro environment should be performed using an Edinburgh Instruments FLS1000 photoluminescence spectrometer outfitted with added capabilities. Samples are excited using either a 450 W xenon arc lamp or a pulsed xenon microsecond flashlamp attached to a double grating Czerny-Turner excitation monochromator. The emission signal is collected at 90° relative to the excitation source and is passed through a single grating Czerny-Turner emission monochromator prior to being collected with an extended red photomultiplier tube (PMT) detector in a cooled housing unit operated at −22° C. A long-pass filter should be placed before the emission monochromator. To test samples at the relevant application temperature, measurements should be done using a water-jacketed cuvette holder maintained at 37° C. via a recirculating bath (RCS 6, Lauda). Custom 3D-printed cuvette inserts are used to mount ~12×12 mm samples within quartz cuvettes. The cuvette insert holds the sample in place along the cuvette diagonal such that the sample is 45° from both the excitation light source and the detector and is in a back-scattered geometry. However, the cuvette insert also functions as a cuvette lid that contains a channel-guided hole for insertion of tubing for gas exchange/bubbling, a hole for insertion of a micro Clark electrode, and a vent hole. After the sample is added to the cuvette insert, mounted samples should be submerged in distilled water and placed under vacuum to remove trapped air, and the mounted sample should remain in distilled water overnight to ensure sufficient hydration. Then, the cuvette insert holding the sample is added to a quartz cuvette containing PBS. The dissolved oxygen concentration in the cuvette should be controlled via gas mixtures introduced to the sample solution with Teflon tubing fed through the cuvette insert. Mass flow controllers (Alicat MC-Series) are used to combine pure nitrogen and a custom air mixture (20.9% $O_2$/79.1% $N_2$) in the appropriate ratios to obtain 0.5, 1, 2, 5, and 10% oxygen at a fixed flow rate of 50 sccm. A needle-based Clark electrode oxygen microsensor (Unisense) should be used to continuously monitor the solution during measurements. For a given dissolved oxygen concentration, the corresponding gas mixture should be bubbled for at least 10 minutes prior to measurement. Intensity should be monitored periodically through the use of short kinetic scans at the peak emission wavelength, while the solution is also monitored simultaneously via the use of the needle-based Clark electrode. Once both the Clark electrode reading and the emission intensity plateau, it is assumed that the sensor is at the target dissolved oxygen concentration. At this point, a phosphorescence lifetime decay can be obtained. Lifetime decays are collected using 4000 data channels and 5000 counts at maximum. To ensure that no unexpected changes in dissolved oxygen concentration occur during the measurement, emission intensity should be reassessed after lifetime collection, and the Clark electrode reading should be continuously monitored throughout the process. This procedure is repeated for all target oxygen concentrations. Instrument response function (IRF) curves are obtained for each decay period by setting the emission wavelength equal to the excitation wavelength, changing the emission intensity to 1% of its maximum, removing the emission filter, and adjusting the excitation and emission bandwidths such that counts per second are <1000. Lifetime fitting should then be performed via a reconvolution fit. Instead of attempting a direct measurement of the hydrated deaerated lifetime ($\tau_0$), an estimated approach should be used due to concerns over the ability to maintain and reach 0 μM dissolved oxygen for these hydrated solid samples at 37° C. Such a sample configuration is not conducive to the standard freeze pump thaw approach that can be utilized for solution samples. The necessity to continuously bubble throughout data collection into a relatively small volume of solution (~2 mL of PBS) is a further hindrance. These obstacles make it difficult to achieve a true 0 μM dissolved oxygen concentration, and for highly sensitive, long-lifetime oxygen sensors, even trace amounts of oxygen could lead to noticeable quenching. Therefore, the predictive method should be utilized which consists of performing a linear regression fit on $1/\tau$ versus dissolved oxygen concentration; for linear Stern-Volmer plots, this intercept equals $1/\tau_0$. Then, the Stern-Volmer plot should be constructed by plotting $\tau_0/\tau$ versus dissolved oxygen concentration, where dissolved oxygen concentration should be calculated by taking into account the concentration of the gas mixture, the solution temperature, and the PBS salinity. If the Stern-Volmer plot is linear, a linear least squares regression should be applied, and the slope of this fit is the Stern-Volmer quenching constant ($K_{SV}$). Then, the bimolecular quenching rate constant ($k_q$) should be calculated by taking into account that $K_{SV}=k_q\tau_0$. Lastly, the dissolved oxygen concentration at which the deaerated lifetime drops to 50% of its maximum value is defined as $1/K_{SV}$. For purposes of this specification, the in vitro oxygen sensing properties of the sensor are $K_{SV}$, $\tau_0$, $k_q$, and $1/K_{SV}$ as determined through analysis of the constructed Stern-Volmer plot for dissolved oxygen sensing in 37° C. PBS.

Test Method 2 Method for Determining Absorption Maxima and Emission Maximum of Oxygen Sensors. The red-most absorption maxima of the chromophore once incorporated into the polymer matrix should be determined by first collecting an excitation spectrum. The excitation spectrum of the chromophore in the solid matrix should be obtained using an Edinburgh Instruments FLS1000 photoluminescence spectrometer. For this measurement, an ~12×12 mm sensor composition should be first mounted in a custom 3D-printed cuvette insert, submerged in distilled water, and placed under vacuum to remove any trapped air. Then, the cuvette insert holding the sample should be added to a quartz cuvette containing PBS. The measurement should involve excitation via a 450 W xenon arc lamp flashlamp attached to a double grating Czerny-Turner excitation monochromator. The emission signal is collected at 90° relative to the excitation source and is passed through a single grating Czerny-Turner emission monochromator prior to being collected with an extended red photomultiplier tube (PMT) detector in a cooled housing unit operated at −22° C. The sample should be oriented 45° from the excitation light and detector in either a back-scattered or front-scattered geometry. A long-pass filter should be placed before the emission monochromator. The measurement should be done using a water-jacketed cuvette holder maintained at 37° C. via a recirculating bath (RCS 6, Lauda). An excitation spectrum should then be obtained for the wavelength corresponding to the emission maximum of the composition. The excitation spectrum should then be examined, and the peaks of the excitation spectrum should be assumed to be equivalent to the absorption maxima. In particular, the wavelength of the red-most absorption maxima should be identified. For determining the emission maximum, an emission spectrum should be obtained using the same FLS1000 system and sample set-up as described for the excitation spectrum measurement. However, in this case, an emission spectrum should be collected by exciting the sensor composition at its red-most absorption maxima. For purposes of this specification, the red-most absorption maxima of the sensor composition should be identified through an excitation spectrum of the sensor obtained in 37° C. PBS, while the emission maximum should be determined from an emission spectrum of the composition in 37° C. PBS.

Test Method 3 Method For Determining Uniformity of Chromophore Distribution. Phosphorescence decay curves obtained at 0.5, 1, 2, 5, and 10% $O_2$ in PBS at 37° C. should be assessed to determine if the chromophore is uniformly dispersed in the polymer matrix. If the individual phosphorescence decays are monoexponential, this observation indicates that the chromophore is in a homogeneous environment. Using the obtained phosphorescence decay curves alongside corresponding IRF curves, reconvolution fits should be performed using Origin software (OriginLab Corporation) and a modified version of OriginLab's "fitconv" algorithm. Specifically, there should be attempts to fit each decay to either a standard monoexponential or biexponential decay function with pre-exponential term(s) and a non-fixed baseline term. A monoexponential decay is deemed to be the most appropriate when the biexponential reconvolution fit fails to converge, offers duplicate lifetimes, or fails to offer significant improvement to the fit or residuals. In addition, a Stern-Volmer plot should be constructed by plotting $\tau_0/\tau$ versus dissolved oxygen concentration. If the Stern-Volmer plot is linear and not downward curving, this is another indicator that the chromophore experienced a homogenous environment in the polymer matrix. Therefore, if individual phosphorescence decay curves are monoexponential and the Stern-Volmer plot is linear, then the chromophore should be determined to have a homogenous environment, indicating that it is uniformly distributed in the polymer matrix. For purposes of this specification, the chromophore distribution is deemed to be uniformly incorporated if phosphorescence decays are monoexponential, and the Stern-Volmer plot is linear.

Test Method 4 Method To Determine In Vitro Sensor Degradation. In vitro aging experiments should be conducted by first ensuring samples contain no trapped air and are thoroughly wetted by submerging them in distilled water and applying a vacuum. Then, samples are transferred to glass vials containing PBS+0.02 wt/vol % sodium azide. These vials should be put in an incubator set to 37° C., and the solution should be exchanged approximately every four weeks. At select time points, samples should be removed from the solution, rinsed thoroughly with distilled water, and then dried for 24 hr under vacuum. The morphology of the samples should be assessed via scanning electron microscopy (SEM). Samples should be weighed, and the mass should be compared to the initial mass. For samples that maintain sufficient physical integrity, the oxygen sensing properties should be reassessed via Test Method 1. For purposes of this specification, the in vitro sensor degradation is assessed by monitoring the fiber morphology, mass, and oxygen sensing properties versus degradation time in 37° C. PBS.

Test Method 5 Method To Determine Weight-average Molecular Weight. The weight-average molecular weight ($M_w$) of copolymers and homopolymers should be characterized by size-exclusion chromatography system in tetrahydrofuran against polystyrene standards. The size-exclusion chromatography system includes an Agilent Technologies 1260 Infinity liquid chromatography interface equipped with a Wyatt Technologies Optilab T-rEX refractive index detector. The copolymer or homopolymer to be tested should be dissolved in high performance liquid chromatography grade tetrahydrofuran at a concentration of 3 mg per mL and filtered through a 0.2 μm polytetrafluoroethylene syringe filter prior to sample injection into the chromatography system. The raw data output from the Wyatt Technologies Optilab T-rEX refractive index detector should be analyzed using the ASTRA 6 software from Wyatt Technologies. Once the column calibration file of polystyrene standards in tetrahydrofuran are loaded into the software, the refractive index baseline of the solution and elution peak range of the polymers are defined, and the software should then be used to calculate M. For purposes of this specification, the weight-average molecular weight of the test copolymer or homopolymer is obtained from size-exclusion chromatography in tetrahydrofuran where the identified elution peak range of the copolymer or homopolymer is compared against the known calibration curve of a polystyrene standard.

Test Method 6. Method To Determine Inherent Viscosity of Copolymer or Homopolymer. Inherent viscosity ($\eta_{inh}$) and relative viscosity ($\eta_r$) should be determined via a Cannon-Ubbelohde viscometer. The viscometer is used in a 30° C. water bath with a minimum bath depth of 25.4 cm with a minimum viscometer submersion depth of 21.6 cm. Polymer solution samples should be prepped at a 0.1 wt/vol % (0.1 g per dL) concentration in 1,1,1,3,3,3-hexafluoro-2-propanol (HFIP) with a minimum sample volume of 11 mL. Relative viscosity is calculated via dividing the flow time (seconds) of the 0.1 wt/vol % solution against neat HFIP solvent flow time in the Cannon-Ubbelohde viscometer between the marked flow lines. For purposes of this specification, the inherent viscosity of the copolymer or homopolymer is the natural log of the relative viscosity divided by the polymer concentration.

Test Method 7. Method To Determine Melting Point of Copolymer or Homopolymer. Differential scanning calorimetry (DSC) should be completed on a TA DSC 2500. Approximately 10 mg of copolymer or homopolymer to be tested should be crimped into Tzero aluminum hermetic pans for thermal analysis. A heat-cool-heat cycle should be applied with a heating rate of 10° C./min. For purposes of this specification, the melting point of the copolymer or homopolymer is the onset of the endothermic peak on the second heating curve.

Test Method 8. Test Method To Determine Fiber Diameter and Pore Length. Prior to fiber diameter and pore length measurements, electrospun scaffolds should first be imaged with a Phenom XL Desktop SEM. First, conductive carbon tape (Ted Pella, Inc.) should be used to mount samples on aluminum SEM stub mounts (Ted Pella, Inc.). Samples should be sputter coated with gold and then imaged with an accelerating voltage of 10 kV. Images of each scaffold should be obtained at a magnification of at least 2000×. Fiber diameter measurements should be performed using Phenom Fibermetric software. At least 100 automated measurements should be obtained and averaged to determine the fiber diameter. Pore length measurements should be performed using either Phenom Fibermetric software or Phenom Image Viewer software. The pore length should be considered to be the longest distance across a pore that is bounded by fibers in the same layer. Considering only the top layer of fibers, at least 12 manual measurements should be obtained and averaged to determine pore length in the top layer of fibers. When necessary to avoid depth-of-field issues, the contrast of the image should be increased to ensure that only the top layer of fibers is considered. For purposes of this specification, the fiber diameter and pore length are the average values determined via analysis of SEM images where only the top layer of fibers is considered for pore length measurements.

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 2A:
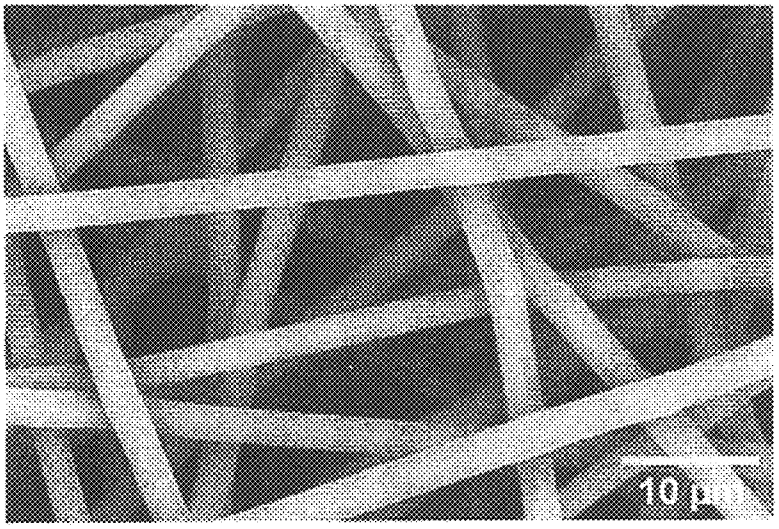
FIG. 2A is the morphology of Pd (II) tetramethacrylated benzoporphyrin (PdBMAP)-containing PDO (mass ratio of PdBMAP to PDO is 1:883.4; scale bar: 10 μm).
Figure 2B:
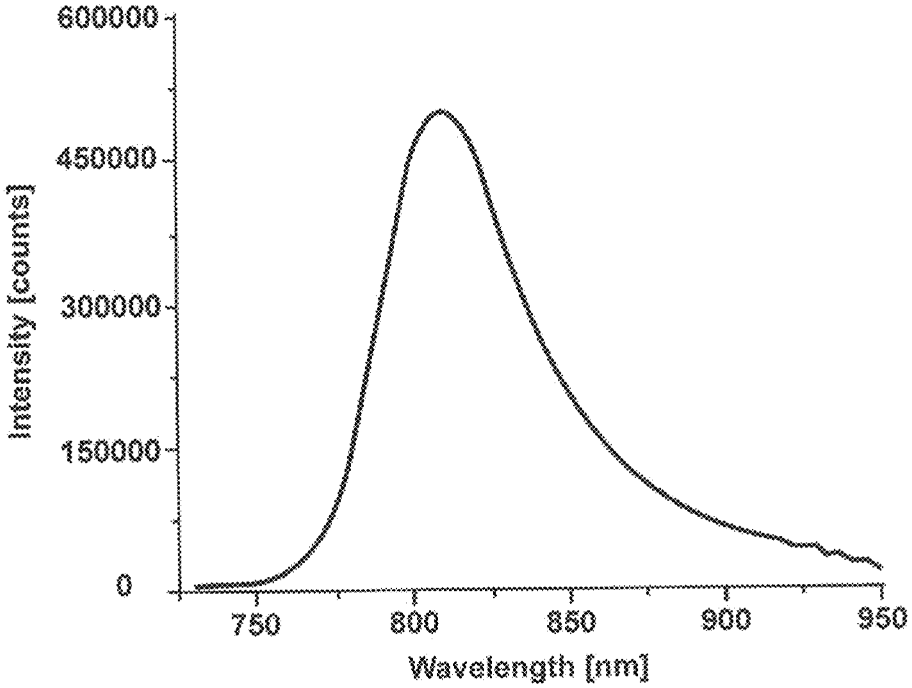
FIG. 2B is an emission spectrum of PdBMAP-containing PDO (mass ratio of PdBMAP to PDO is 1:883.4) in aerated phosphate-buffered saline (PBS) at 37° C.
Figure 2C:
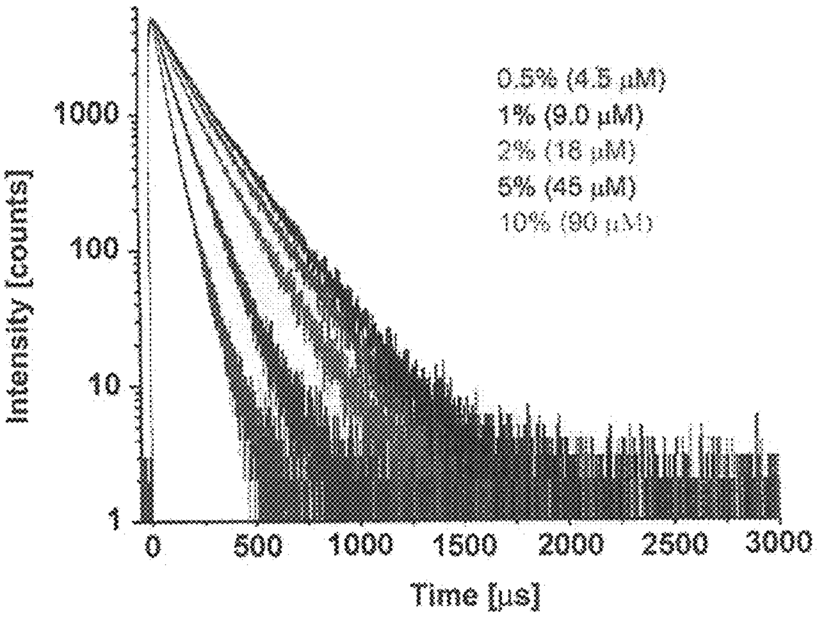
FIG. 2C is phosphorescence decay curves of PdBMAP-containing PDO (mass ratio of PdBMAP to PDO is 1:883.4) at various dissolved oxygen concentrations in 37° C. PBS.
Figure 2D:
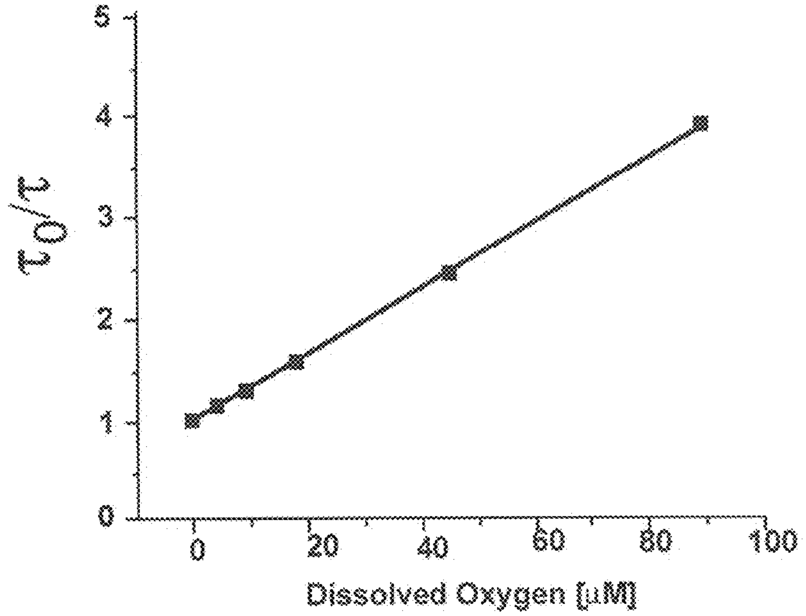
FIG. 2D is a Stern-Volmer plot of PdBMAP-containing PDO (mass ratio of PdBMAP to PDO is 1:883.4) in 37° C. PBS.
Figure 3A:
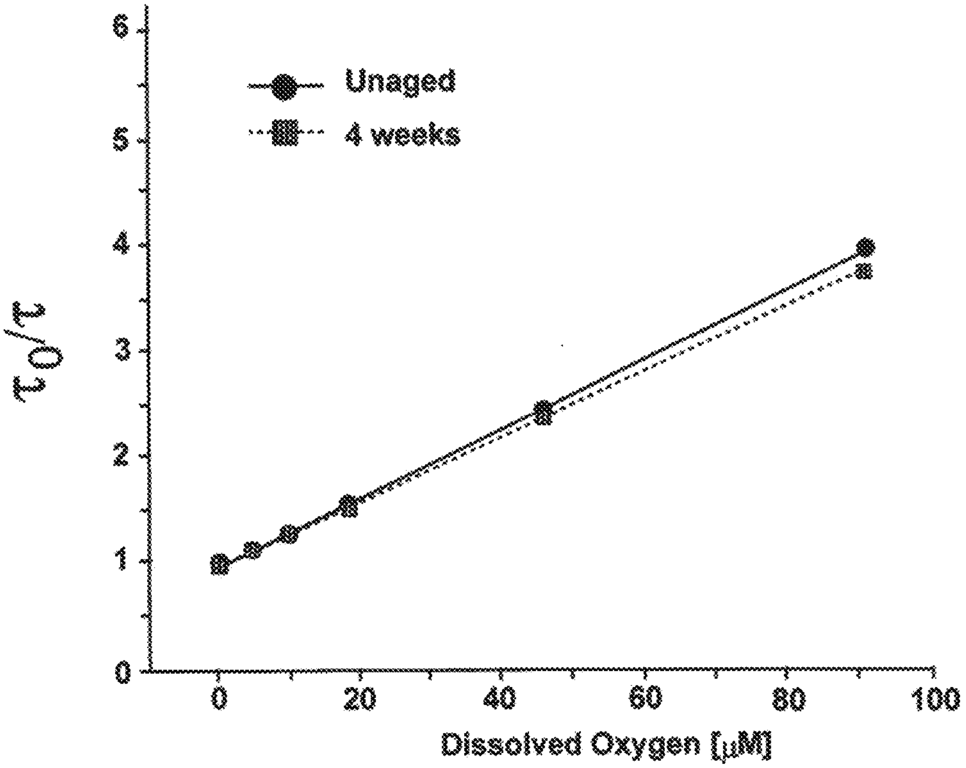
FIG. 3A is the sensor performance of PdBMAP-containing PDO (mass ratio of PdBMAP to PDO is 1:883.4) as a function of degradation time in 37° C. PBS.
Figure 3B:
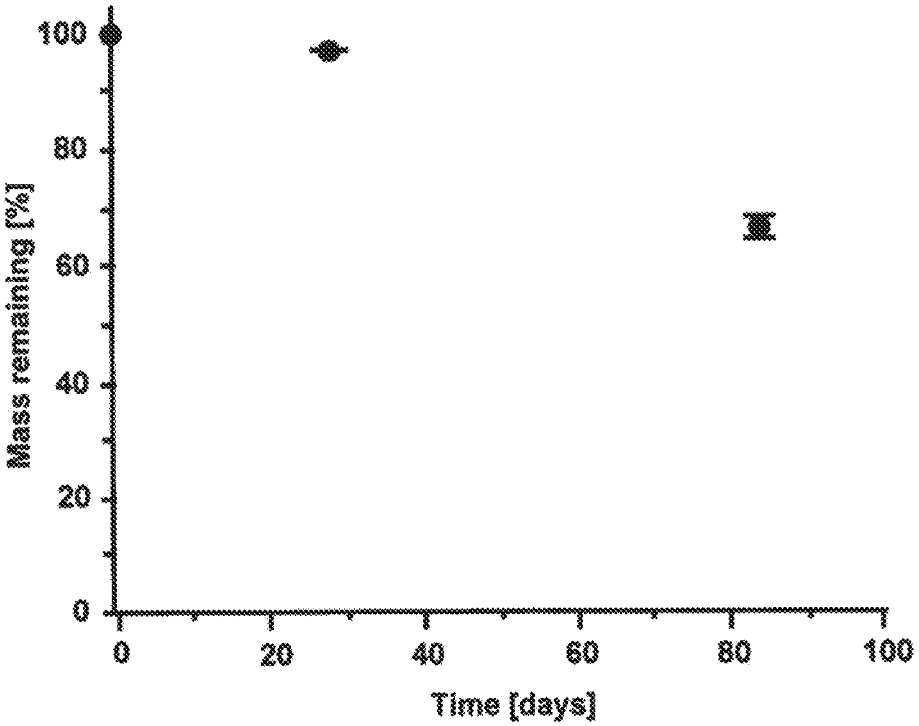
FIG. 3B is the mass loss of PdBMAP-containing PDO (mass ratio of PdBMAP to PDO is 1:883.4) as a function of degradation time in 37° C. PBS.
Figure 3C:
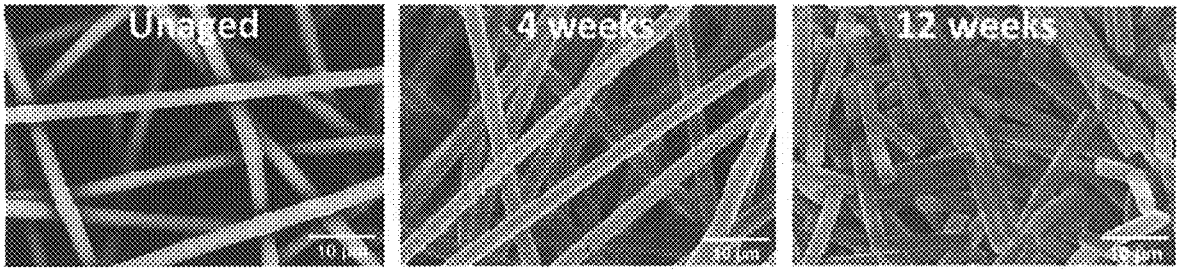
FIG. 3C is the morphology of PdBMAP-containing PDO (mass ratio of PdBMAP to PDO is 1:883.4) as a function of degradation time in 37° C. PBS (scale bar: 10 μm).

Example 1. Process of making and testing a sensor comprising a chromophore and a polymer matrix. An instance of this invention was electrospun poly(p-dioxanone) that contained PdBMAP such that PdBMAP was present at a mass ratio of PdBMAP to PDO of 1:883.4. The polymer was obtained from Evonik (Resomer® X 206 S) and was determined to have a melting point of 95° C. (FIG. 1) and an $\eta_{inh}$ of 1.8 dL/g. To fabricate the electrospun composition, PDO and PdBMAP were dissolved into HFIP such that there was 10 wt % PDO in HFIP. During electrospinning with a Fluidnatek LE-series machine, the solution was extruded at 2.0 mL/hr through a 20 gauge needle. Applied voltages on the needle and collecting substrate were +10 and −0.5 kV, respectively. There was 18 cm between the needle and collector. The collector was a cylinder that was rotated with a linear velocity of ~262 cm/s, and the emitter translated along the width of the collector at a rate of 10 mm/s. Environmental conditions were set to 25° C. and 40% relative humidity. After electrospinning, the scaffold was placed under vacuum for 24 hours to remove residual solvent. The morphology is shown in FIG. 2A; the average fiber diameter was ~3.1 μm, and the average pore length was ~23 μm. As characterized in 37° C. PBS, the sensor exhibited an emission maximum of ~810 nm (FIG. 2B), a red-most absorption maxima of ~630 nm, a $\tau_0$ of 196 μs, a $K_{SV}$ of $3.2\times10^4$ $M^{-1}$, and a $k_q$ of $1.7\times10^8$ $M^{-1}s^{-1}$. The phosphorescence decays were monoexponential (FIG. 2C), and the Stern-Volmer plot was linear (FIG. 2D). This indicates the likelihood for a homogenous chromophore environment. In addition, both attributes are advantageous for real-time continuous monitoring of tissue oxygen levels. Furthermore, $1/K_{SV}$ was equal to 31 μM dissolved oxygen. This parameter represents the value where the lifetime drops to 50% of its deaerated value, and therefore, gives an idea of the regime where the sensor best functions. Since 31 μM falls within expected physiological levels, the composition exhibited a good dynamic range and would be particularly well-suited for detection of healthy physiological levels and/or sensing hyperoxia. Since phosphorescence lifetime and dissolved oxygen concentration are inversely proportional, a higher sensitivity would be advantageous for detecting hypoxia, but the dynamic range could suffer accordingly. PDO is a bioresorbable polymer and is expected to fully degrade within 3-6 months. In vitro degradation experiments showed that oxygen sensing properties were minimally affected by 4 weeks of aging in 37° C. PBS (FIG. 3A, $\tau_0$ remained 196 μs, $K_{SV}$ changed from $3.2\times10^4$ to $3.1\times10^4$ $M^{-1}$, $k_q$ changed from $1.7\times10^8$ to $1.6\times10^8$ $M^{-1}s^{-1}$). The composition exhibited substantial weight loss (FIG. 3B, 66.3% of initial mass remaining) and significant fiber fragmentation after 12 weeks (FIG. 3C). Although mass loss and morphology changes were assessed at 12 weeks, the oxygen sensing performance could not be assessed as the sample was already fragmented. After this point, the sample could no longer be recovered as a result of further fragmentation.

Figure 4A:
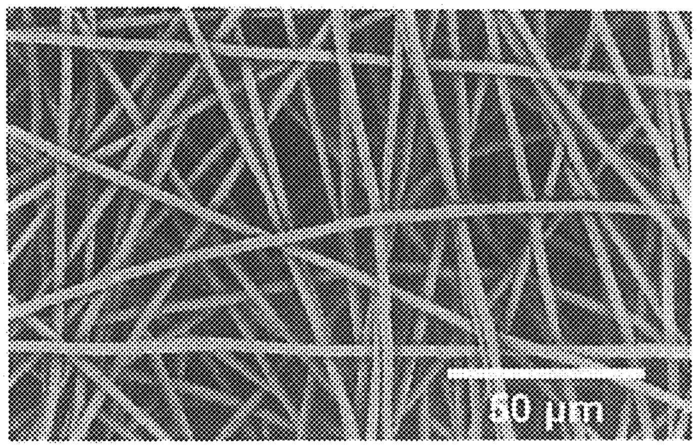
FIG. 4A is the morphology of PdBMAP-containing PDO (mass ratio of PdBMAP to PDO is 1:148.7; scale bar: 50 μm).
Figure 4B:
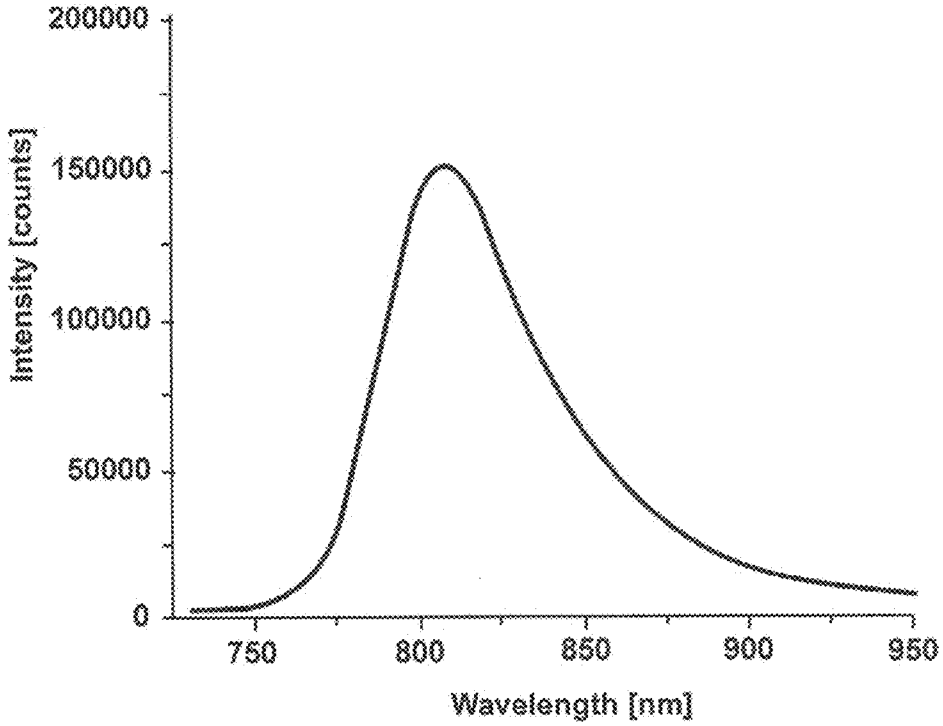
FIG. 4B is an emission spectrum of PdBMAP-containing PDO (mass ratio of PdBMAP to PDO is 1:148.7) in aerated PBS at 37° C.
Figure 4C:
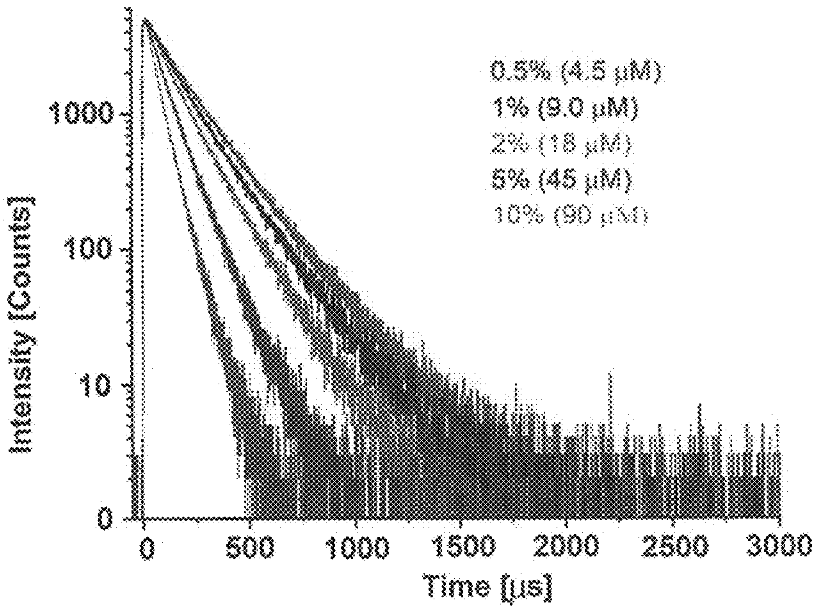
FIG. 4C is phosphorescence decay curves of PdBMAP-containing PDO (mass ratio of PdBMAP to PDO is 1:148.7) at various dissolved oxygen concentrations in 37° C. PBS.
Figure 4D:
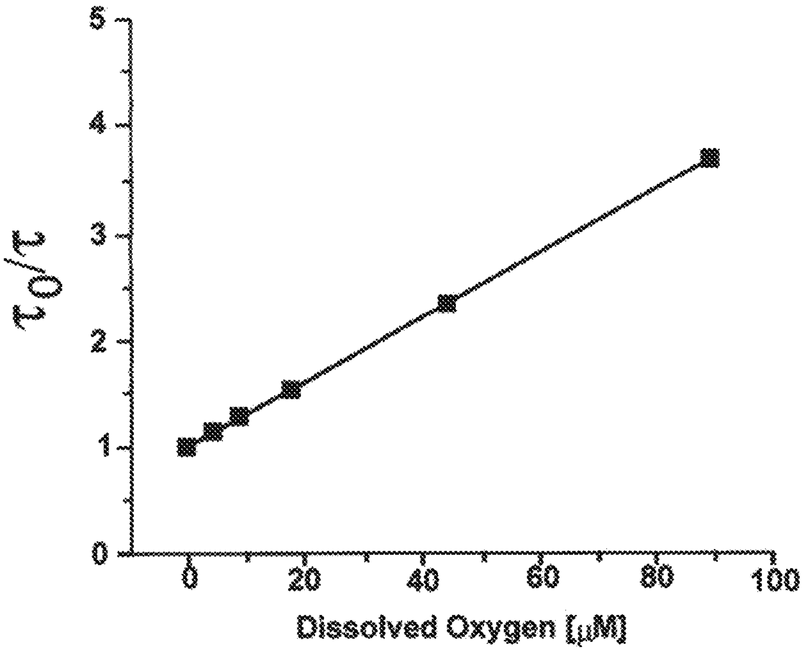
FIG. 4D is a Stern-Volmer plot of PdBMAP-containing PDO (mass ratio of PdBMAP to PDO is 1:148.7) in 37° C. PBS.

Example 2. Process of making and testing a sensor comprising a chromophore and a polymer matrix. Another instance of this invention was electrospun PDO+PdBMAP for which PdBMAP was present at a mass ratio of PdBMAP to PDO of 1:148.7. With the exception of the altered chromophore concentration, fabrication of the scaffold was identical to as described in Example 1. The fiber morphology is shown in FIG. 4A. The average diameter was ~3.0 μM, and the pore length was ~22 μM. In 37° C. PBS, the sensor exhibited an emission maximum of ~810 nm (FIG. 4B), a red-most absorption maxima of ~630 nm, a $\tau_0$ of 185 μs, a $K_{SV}$ of $3.0\times10^4$ $M^{-1}$, a $k_q$ of $1.6\times10^8$ $M^{-1}s^{-1}$, and a $1/K_{SV}$ of 33 μM dissolved oxygen. With this increase in chromophore concentration compared to the composition in Example 1 with a mass ratio of PdBMAP to PDO of 1:883.4, the oxygen sensing properties remained very similar. Additionally, the phosphorescence decay curves remained monoexponential (FIG. 4C), while the Stern-Volmer plot remained linear (FIG. 4D). These results indicate that there were no detrimental effects from increasing the chromophore concentration. Therefore, chromophore concentration could be increased to be as high as a mass ratio of PdBMAP to PDO of 1:148.7 to improve the emission intensity without experiencing significant changes in sensor performance.

Figure 5A:
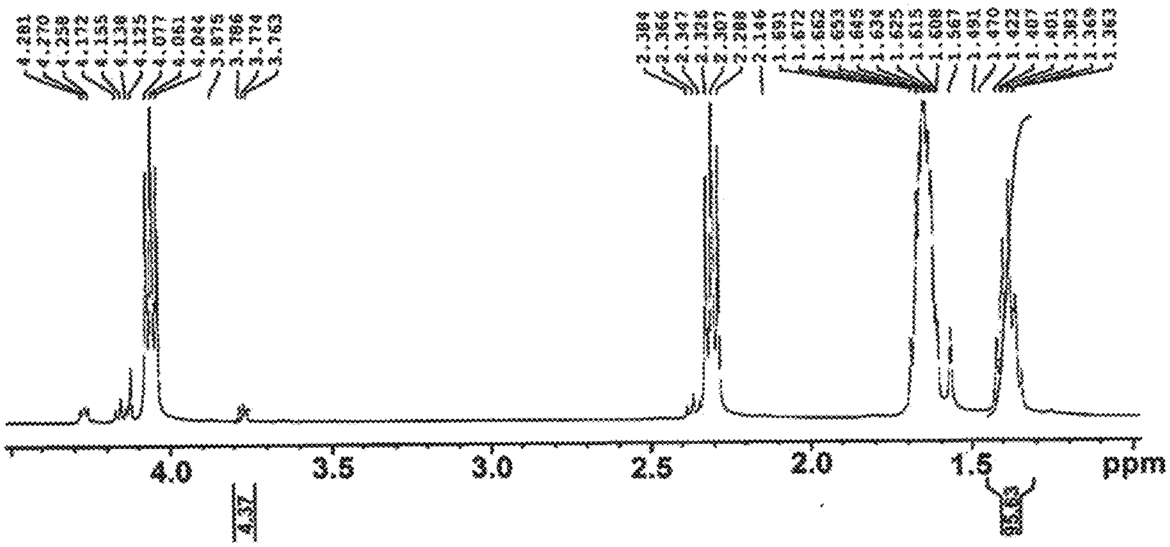
FIG. 5A is a $^1$H nuclear magnetic resonance (NMR) spectrum of poly(ε-caprolactone-co-p-dioxanone) (P(CL-co-DO)) with targeted 5 mol % of p-dioxanone.
Figure 5B:
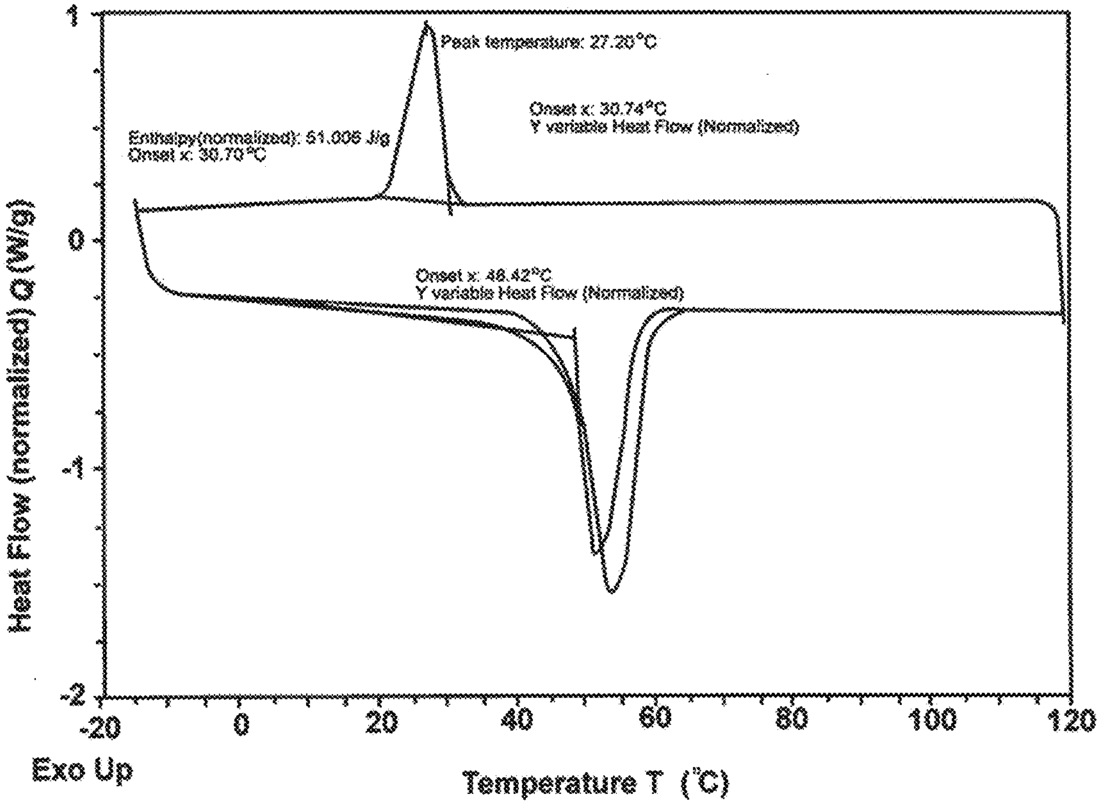
FIG. 5B is differential scanning calorimetry curves of P(CL-co-DO) with targeted 5 mol % of p-dioxanone.
Figure 6A:
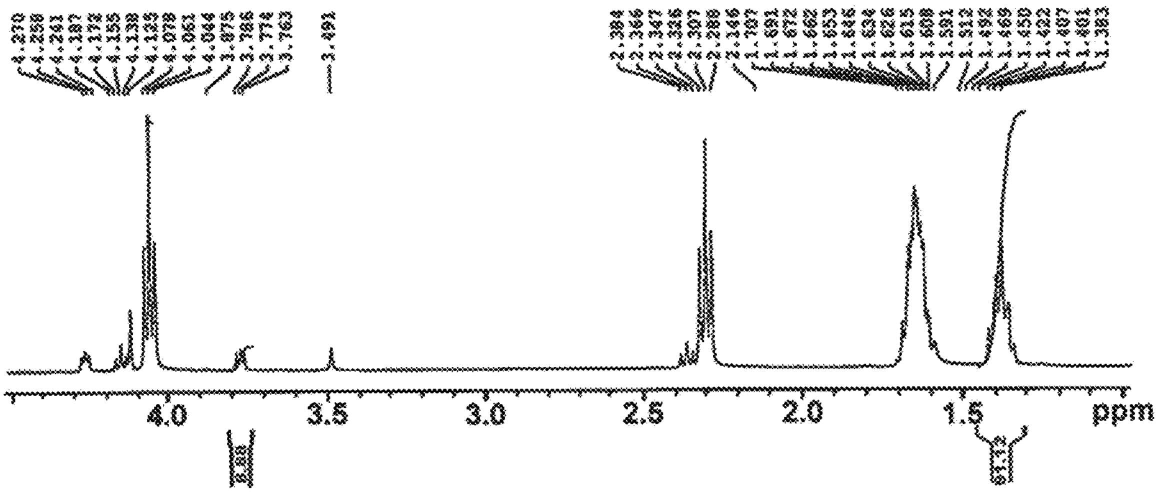
FIG. 6A is a $^1$H NMR spectrum of P(CL-co-DO) with targeted 10 mol % of p-dioxanone.
Figure 6B:
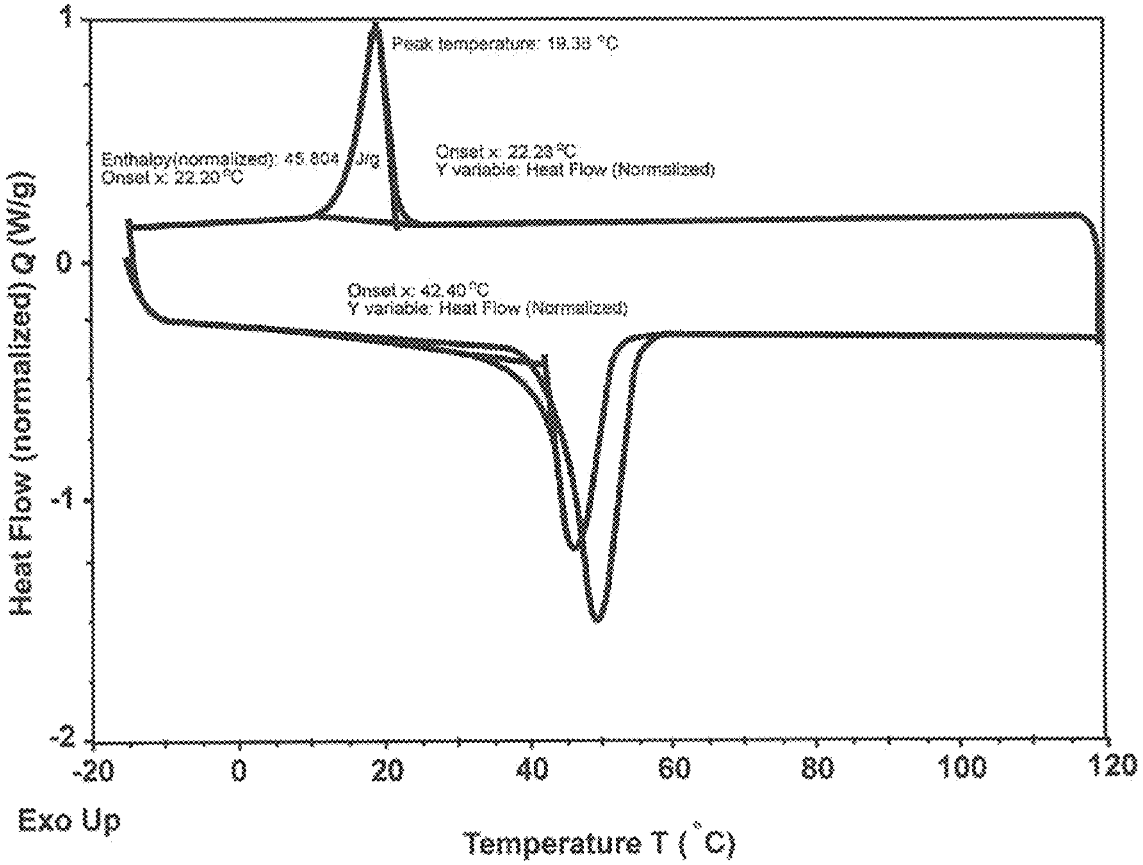
FIG. 6B is differential scanning calorimetry curves of P(CL-co-DO) with targeted 10 mol % of p-dioxanone.

Example 3. Process of making a polymer for use in a sensor. Instances of the invention were also produced in which the polymer matrix was the copolymer poly(ε-caprolactone-co-p-dioxanone). In these instances, synthesis of P(CL-co-DO) with varying mole percentage of p-dioxanone was conducted via random, ring-opening copolymerization of ε-caprolactone and p-dioxanone in neat monomer with ethylene glycol as the initiating species and tin (II) 2-ethylhexanoate as the reaction catalyst at 130° C. for 48 hours under oxygen and moisture free conditions. Targeted molecular composition of P(CL-co-DO) random copolymers included 10 mol % and 5 mol % of p-dioxanone with the respective 90 mol % and 95 mol % of ε-caprolactone. In general, these compositions will, hereafter, be referred to as 90:10 P(CL-co-DO) and 95:5 P(CL-co-DO) according to their targeted molecular compositions. Copolymer with $M_w$ greater than 75,000 Da were targeted for use in the electrospinning processing. P(CL-co-DO) copolymers with molecular weights meeting the target were afforded via having very low amounts of the initiating species, ethylene glycol, relative to the two monomers, ε-caprolactone and p-dioxanone, during the reaction polymerization. The initiator to total monomer mole ratio used was 1:200. The catalyst to total monomer mole ratio used was 1:17,000. Copolymerization reactions were also moisture free to minimize or prevent any hydrolytic degradation and oxygen free to prevent oxidation of the tin (II) 2-ethylhexanote ($Sn(Oct)_2$) catalyst. Moisture and oxygen free conditions were afforded by using oven dried or flame dried reaction flasks under inert atmosphere. Inert atmospheres included pure nitrogen, pure argon, or under very low vacuum (<1 torr). $^1H$ NMR and DSC data for a representative synthesized 95:5 P(CL-co-DO) copolymer are shown in FIGS. 5A and 5B, respectively. $^1H$ NMR and DSC data for a representative synthesized 90:10 P(CL-co-DO) copolymer are shown in FIGS. 6A and 6B, respectively. The molecular composition of targeted copolymers was determined by comparing the characteristic III NMR peak integration of p-dioxanone (3.786-3.763 ppm) to ε-caprolactone (1.422-1.363 ppm). Below is a general reaction random copolymerization scheme of ε-caprolactone and p-dioxanone to form P(CL-co-DO) with ethylene glycol as the initiator and $Sn(Oct)_2$ as the catalyst.

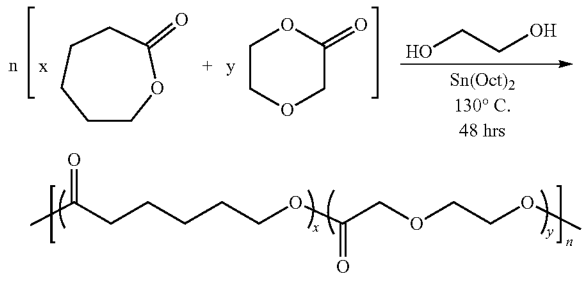

P(CL-co-DO)

Figure 7A:
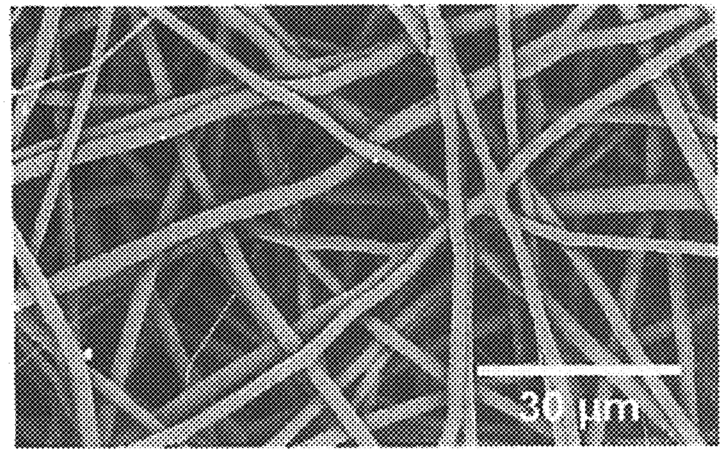
FIG. 7A is the morphology of PdBMAP-containing 95:5 P(CL-co-DO) (mass ratio of PdBMAP to P(CL-co-DO) is 1:247.8; scale bar: 30 μm).
Figure 7B:
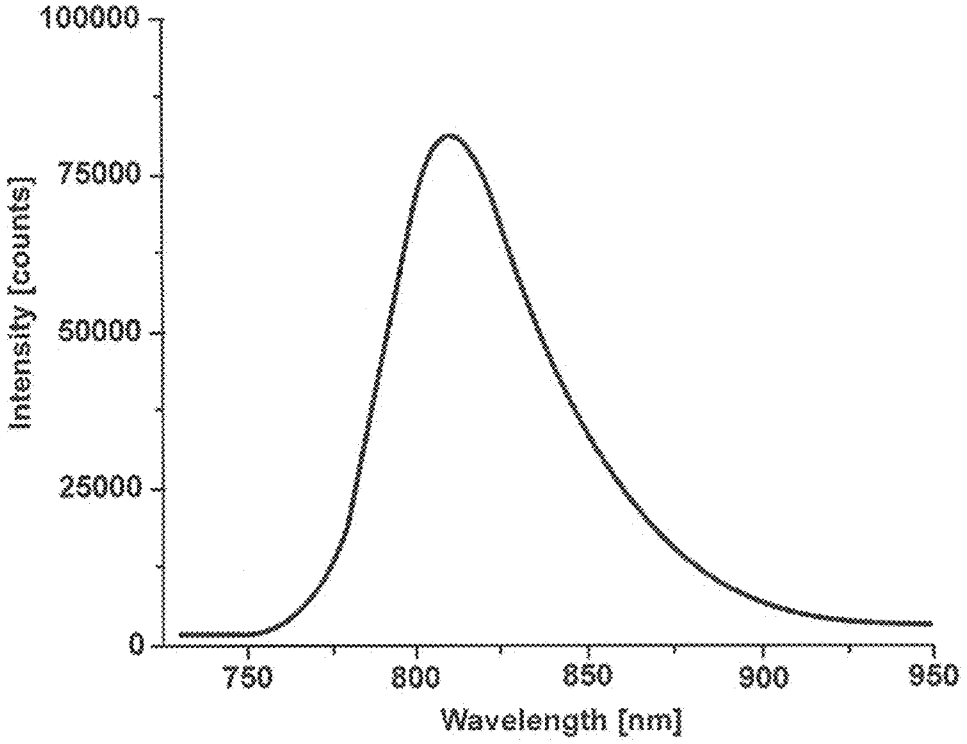
FIG. 7B is an emission spectrum of PdBMAP-containing 95:5 P(CL-co-DO) (mass ratio of PdBMAP to P(CL-co-DO) is 1:247.8) in aerated PBS at 37° C.
Figure 7C:
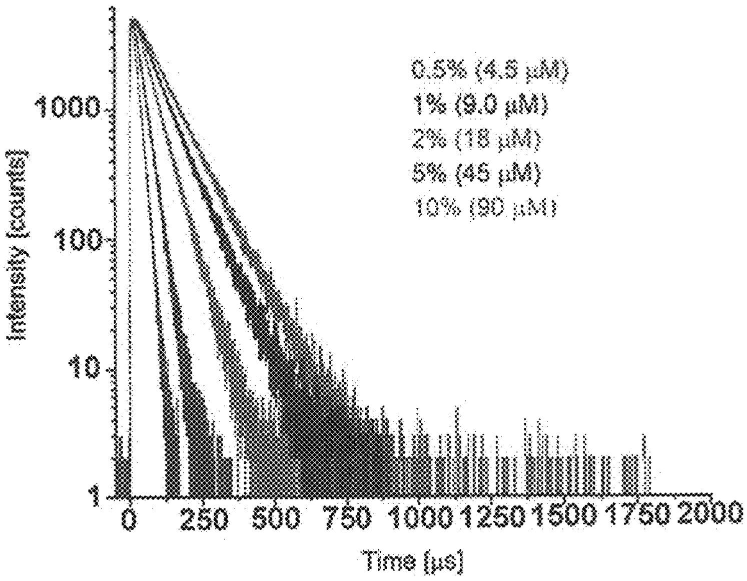
FIG. 7C is phosphorescence decay curves of PdBMAP-containing 95:5 P(CL-co-DO) (mass ratio of PdBMAP to P(CL-co-DO) is 1:247.8) at various dissolved oxygen concentrations in 37° C. PBS.
Figure 7D:
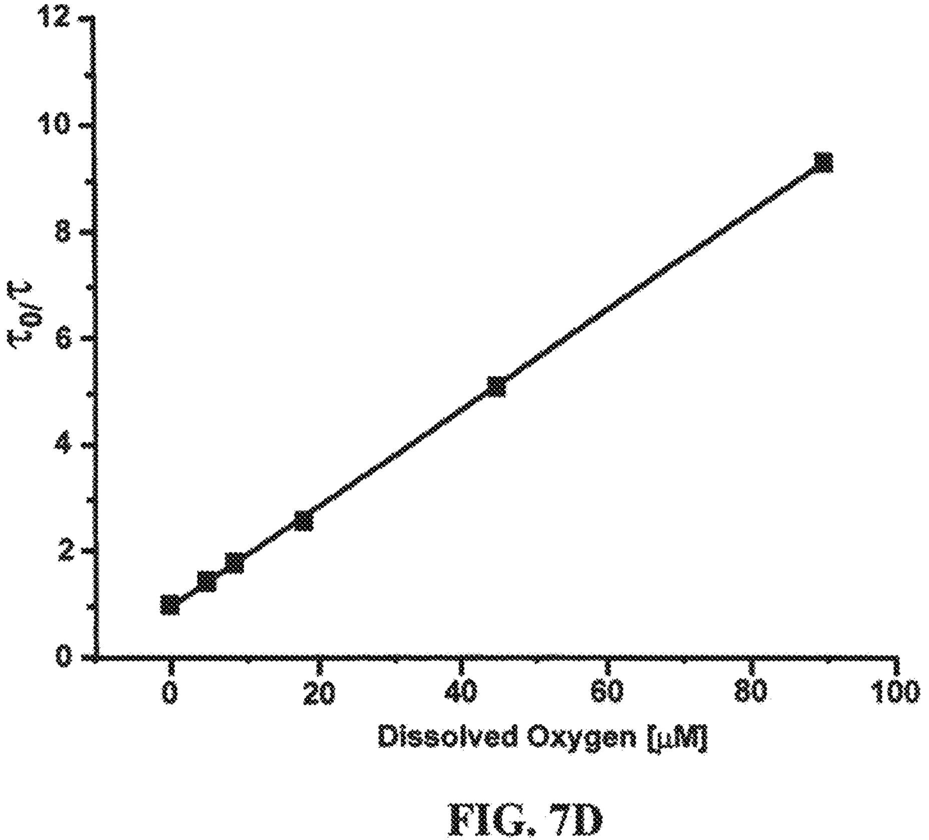
FIG. 7D is a Stern-Volmer plot of PdBMAP-containing 95:5 P(CL-co-DO) (mass ratio of PdBMAP to P(CL-co-DO) is 1:247.8) in 37° C. PBS.
Figure 8A:
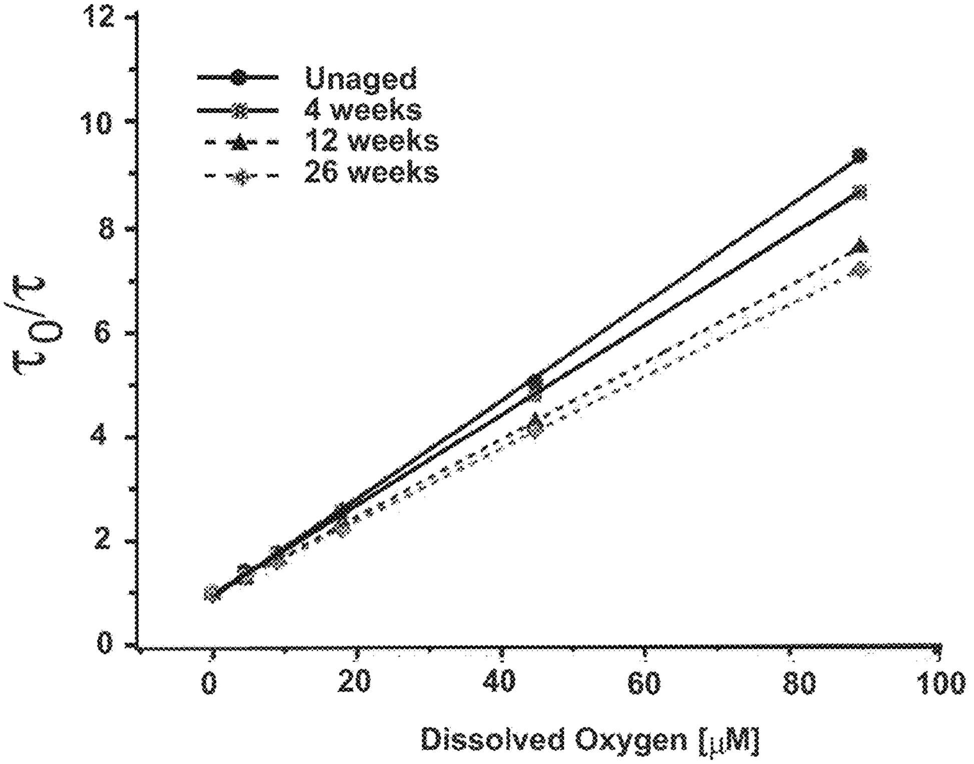
FIG. 8A is the sensor performance of PdBMAP-containing 95:5 P(CL-co-DO) (mass ratio of PdBMAP to P(CL-co-DO) is 1:247.8) as a function of degradation time in 37° C. PBS.
Figure 8B:
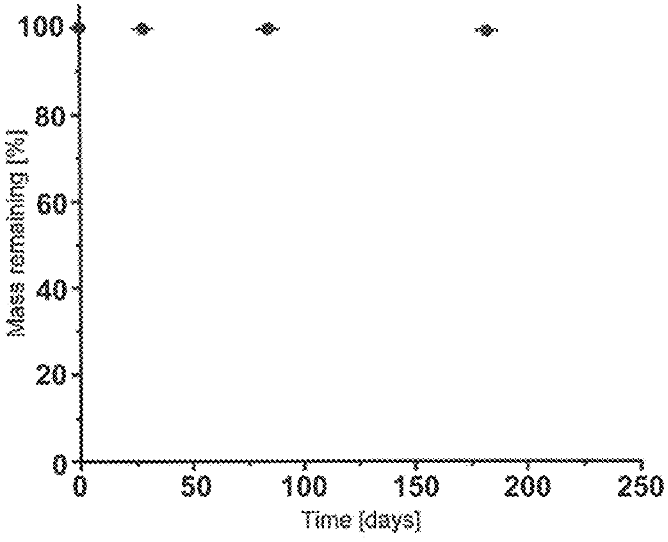
FIG. 8B is the mass loss of PdBMAP-containing 95:5 P(CL-co-DO) (mass ratio of PdBMAP to P(CL-co-DO) is 1:247.8) as a function of degradation time in 37° C. PBS.
Figure 8C:
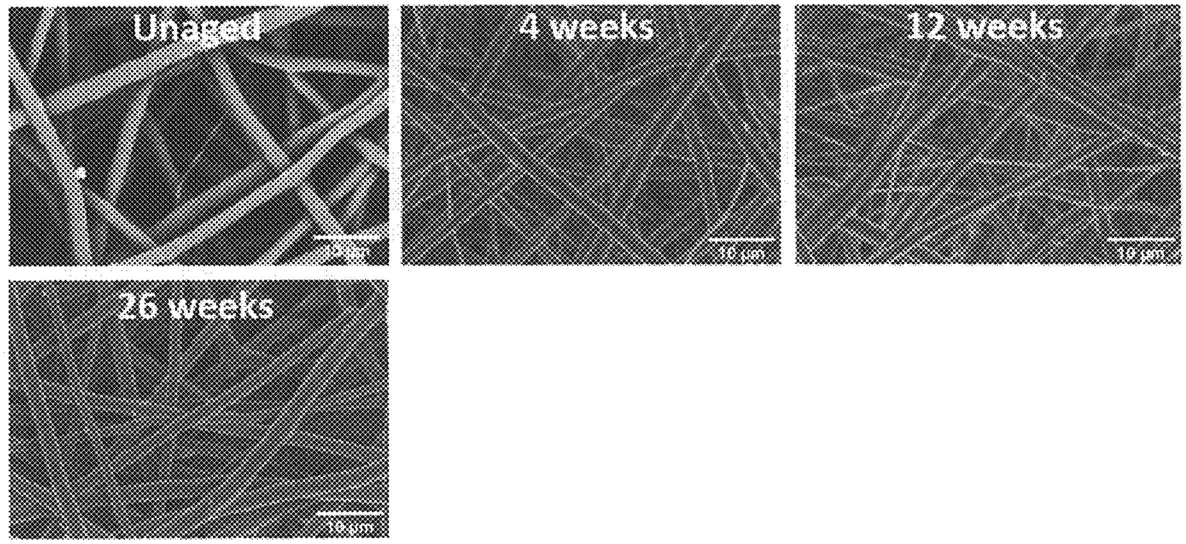
FIG. 8C is the morphology of PdBMAP-containing 95:5 P(CL-co-DO) (mass ratio of PdBMAP to P(CL-co-DO) is 1:247.8) as a function of degradation time in 37° C. PBS (scale bar: 10 μm).

Example 4. Process of making and testing a sensor comprising a chromophore and a polymer matrix. An example of this invention was electrospun 95:5 P(CL-co-DO) that contained PdBMAP at a mass ratio of PdBMAP to P(CL-co-DO) of 1:247.8. P(CL-co-DO) with 5 mol % of p-dioxanone was synthesized as described earlier and had a $M_W$ of 118,000 Da and a melting point of 48° C. To fabricate electrospun samples using a Fluidnatek LE-series electrospinning machine, 95:5 P(CL-co-DO) and PdBMAP were dissolved into 3:1 wt:wt HFIP:dichloromethane (DCM) such that there was 14 wt % P(CL-co-DO) in the solvent mixture. The solution was extruded at 3.0 mL/hr through a syringe with a 20-gauge needle. Applied emitter and collector voltages were +9.0 and −3.5 kV, respectively. There was a 21 cm collection distance, and the cylindrical collector was rotated at a linear velocity of ~105 cm/s. The emitter translated along the width of the collector at a rate of 10 mm/s. The temperature and humidity were controlled to be 25° C. and 40% relative humidity. After electrospinning, the scaffold was placed under vacuum for 24 hours to remove residual solvent. The fiber morphology is shown in FIG. 7A; the average fiber diameter and pore length were ~2.3 and ~22 μm, respectively. After characterization in 37° C. PBS, the emission maximum was ~810 nm (FIG. 7B), the red-most absorption maxima was ~630 nm, the deaerated lifetime was 128 μs, $K_{SV}$ was $9.2\times10^4$ $M^{-1}$, and $k_q$ was $7.2\times10^8$ $M^{-1}s^{-1}$. The monoexponential decay curves (FIG. 7C) and linear Stern-Volmer plot (FIG. 7D) indicate that this composition is well-suited for continuous real-time monitoring. This composition exhibited a $1/K_{SV}$ of 11 μM dissolved oxygen, which indicates that the composition was particularly well-suited for detection or monitoring of hypoxia. In this manner, the composition exhibits a significantly higher sensitivity than the PDO compositions, while the PDO compositions exhibited a greater dynamic range. Considering that poly(ε-caprolactone) has a longer degradation time than PDO (~2-3 years versus ~3-6 months, respectively), it is expected that this PCL-PDO copolymer should have a longer degradation time than the PDO composition which may increase its performance life span. In vitro degradation experiments were conducted for 26 weeks in 37° C. PBS. Oxygen sensor functionality was retained for 26 weeks (FIG. 8A). Although the Stern-Volmer plot remained linear, sensitivity may decrease as a function of aging time. Mass loss (FIG. 8B) and morphological changes (FIG. 8C) observed over this time period were minor. However, after 26 weeks, the sample appeared fragile and would easily tear or fragment if not handled in a sufficiently gentle manner.

Figure 9A:
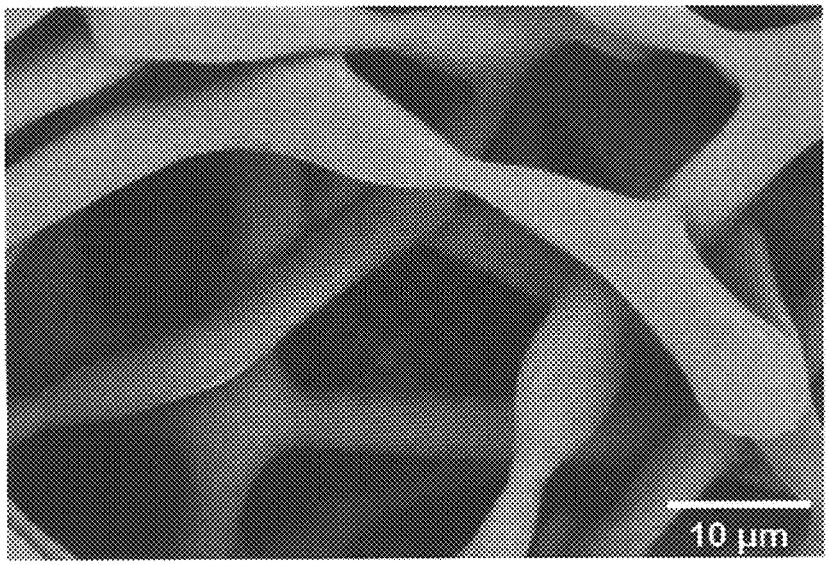
FIG. 9A is the morphology of PdBMAP-containing 90:10 P(CL-co-DO) (mass ratio of PdBMAP to P(CL-co-DO) is 1:247.8; scale bar: 10 μm) that was fabricated as described in Example 5.
Figure 9B:
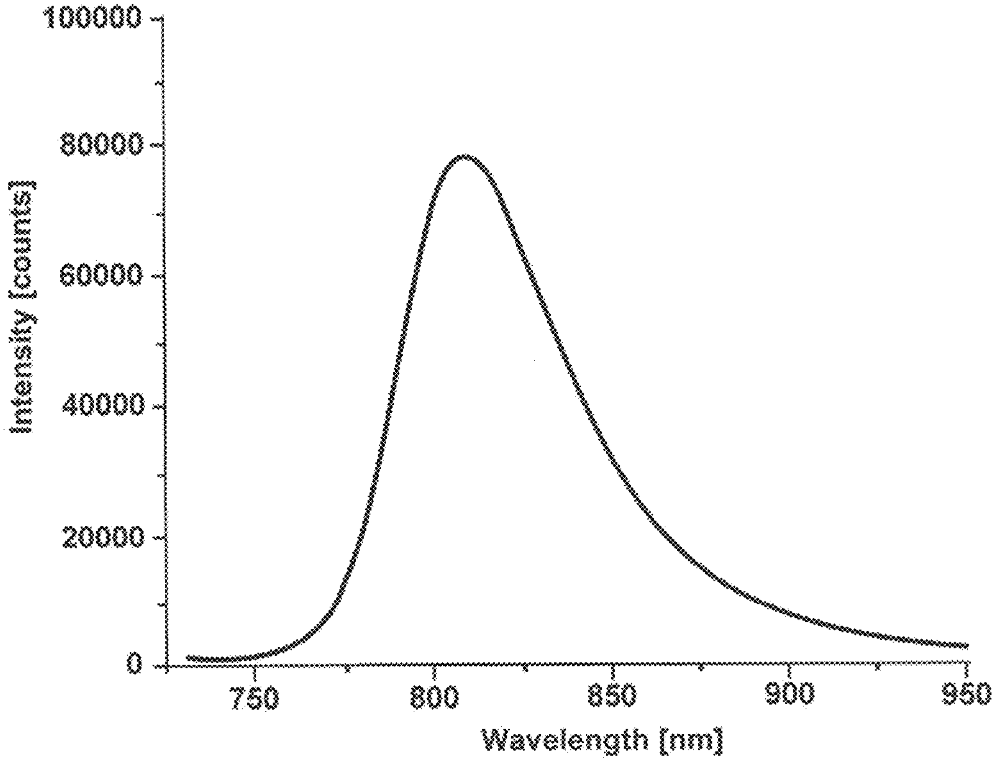
FIG. 9B is an emission spectrum in aerated PBS at 37° C. of PdBMAP-containing 90:10 P(CL-co-DO) (mass ratio of PdBMAP to P(CL-co-DO) is 1:247.8) that was fabricated as described in Example 5.
Figure 9C:
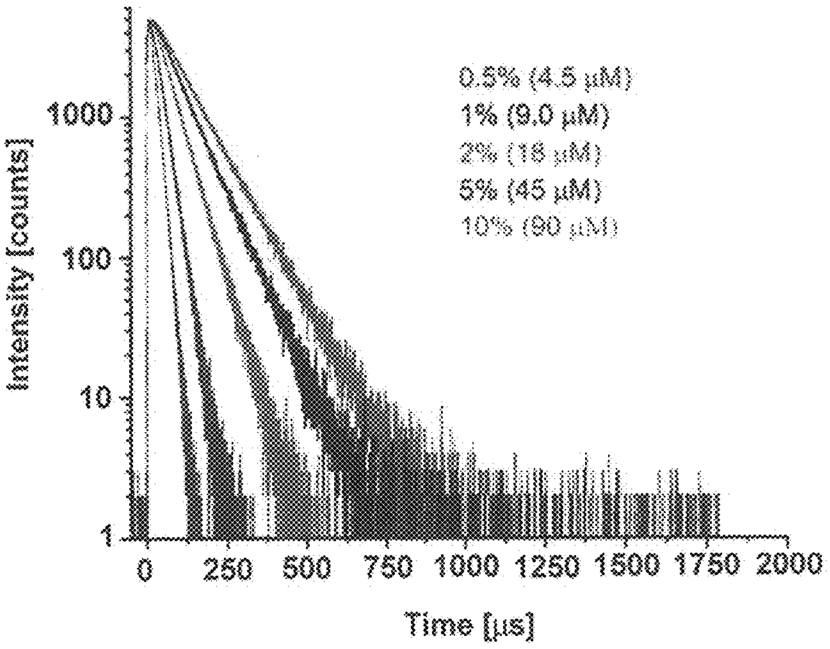
FIG. 9C is phosphorescence decay curves at various dissolved oxygen concentrations in 37° C. PBS of PdBMAP-containing 90:10 P(CL-co-DO) (mass ratio of PdBMAP to P(CL-co-DO) is 1:247.8) that was fabricated as described in Example 5.
Figure 9D:
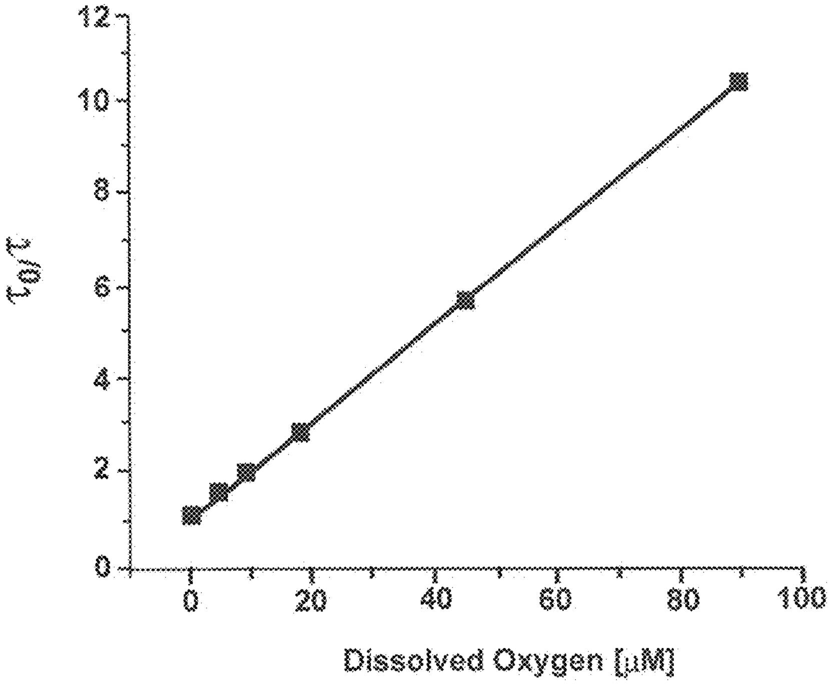
FIG. 9D is a Stern-Volmer plot in 37° C. PBS of PdBMAP-containing 90:10 P(CL-co-DO) (mass ratio of PdBMAP to P(CL-co-DO) is 1:247.8) that was fabricated as described in Example 5.

Example 5. Process of making and testing a sensor comprising a chromophore and a polymer matrix. Another example of this invention was electrospun 90:10 P(CL-co-DO) that contained PdBMAP at a mass ratio of PdBMAP to P(CL-co-DO) of 1:247.8. The P(CL-co-DO) with 10 mol % of p-dioxanone used in this example had a $M_W$ of 133,500 Da and a melting point of 42° C. To electrospin this composition using a Fluidnatek LE-series machine, the polymer and chromophore were dissolved into 1:3 wt:wt HFIP:DCM such that were was 14 wt % 90:10 P(CL-co-DO) relative to the solvent. The solution was pushed through a 20-gauge needle at a flowrate of 4.0 mL/hr. Applied voltages were +8.0 kV to the needle tip and −2.5 kV to a cylindrical collector rotated at a linear velocity of ~105 cm/s. There was an emitter/collector distance of 21 cm. Temperature was controlled to remain at 25° C., while relative humidity was controlled to be 40%. The speed of translation for the needle along the width of the collector was 10 mm/s. The electrospun scaffold was placed under vacuum for 24 hours to remove residual solvent. The morphology is shown in FIG. 9A, and the average fiber diameter and pore length were ~4.1 and ~26 μm, respectively. After characterization in 37° C. PBS, the composition was observed to exhibit an emission maximum of ~810 nm (FIG. 9B), a red-most absorption maxima of ~630 nm, a $\tau_0$ of 147 μs, a $K_{SV}$ of $1.0\times10^5$ $M^{-1}$, a $k_q$ of $7.2\times10^8$ $M^{-1}s^{-1}$, and a $1/K_{SV}$ of 10 μM dissolved oxygen. Decay curves were observed to be monoexponential (FIG. 9C), while the Stern-Volmer plot was linear (FIG. 9D). Overall, properties were similar to those observed for 95:5 P(CL-co-DO)+PdBMAP (mass ratio of PdBMAP to P(CL-co-DO) of 1:247.8). The higher PDO content of this 90:10 P(CL-co-DO) composition should result in a shorter degradation time compared to 95:5 P(CL-co-DO).

Figure 10A:
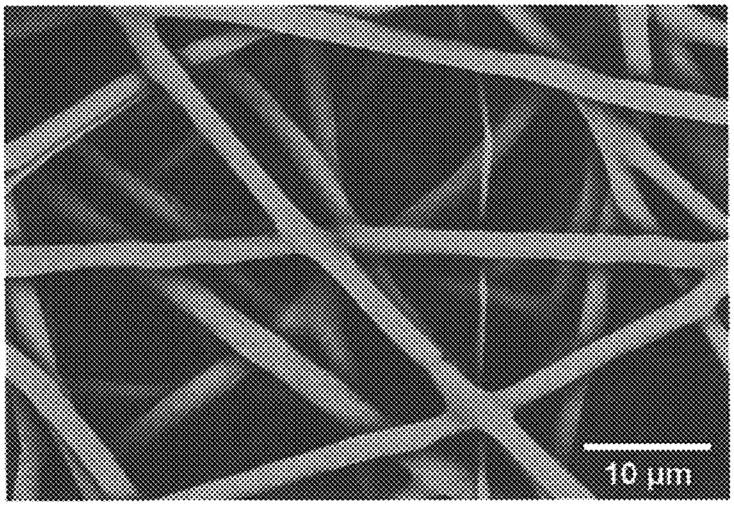
FIG. 10A is the morphology of PdBMAP-containing 90:10 P(CL-co-DO) (mass ratio of PdBMAP to P(CL-co-DO) is 1:247.8; scale bar: 10 μm) that was fabricated as described in Example 6.
Figure 10B:
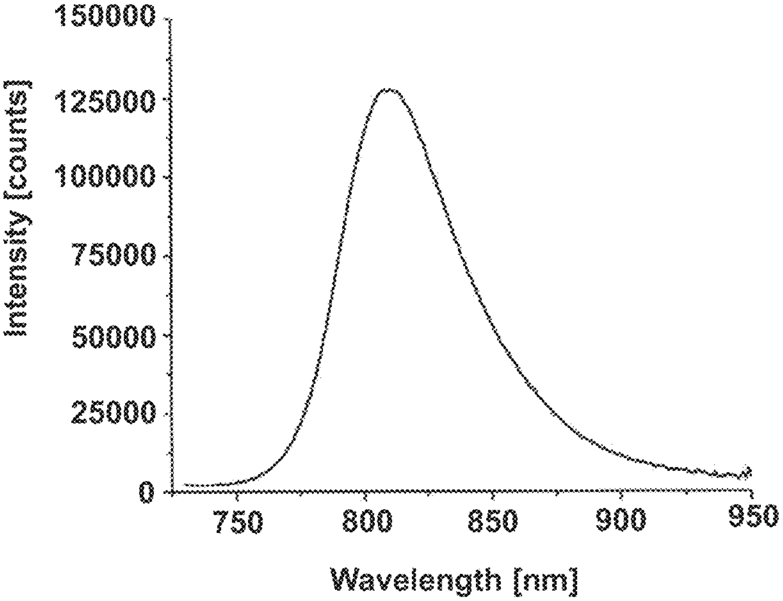
FIG. 10B is an emission spectrum in aerated PBS at 37° C. of PdBMAP-containing 90:10 P(CL-co-DO) (mass ratio of PdBMAP to P(CL-co-DO) is 1:247.8) that was fabricated as described in Example 6.
Figure 10C:
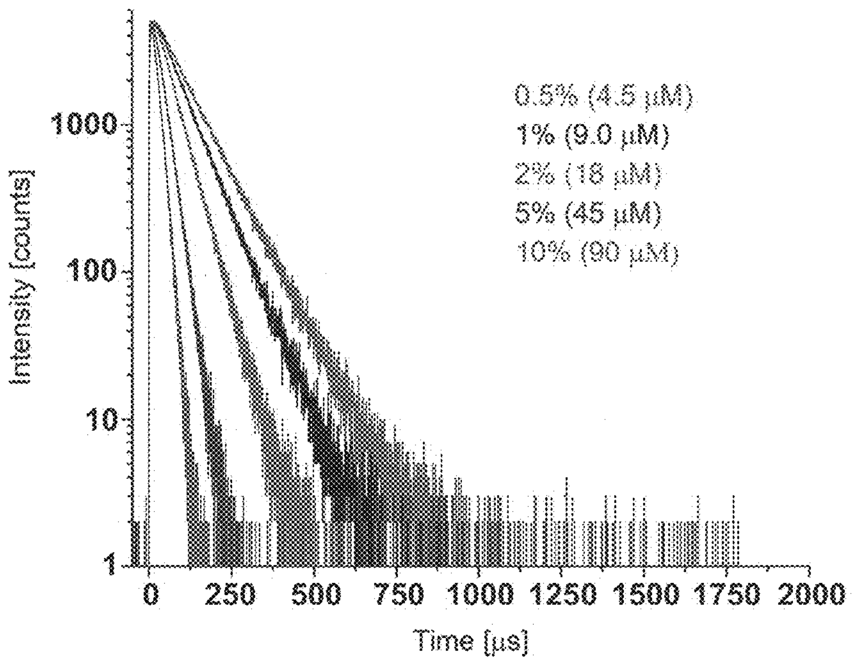
FIG. 10C is phosphorescence decay curves at various dissolved oxygen concentrations in 37° C. PBS of PdBMAP-containing 90:10 P(CL-co-DO) (mass ratio of PdBMAP to P(CL-co-DO) is 1:247.8) that was fabricated as described in Example 6.
Figure 10D:
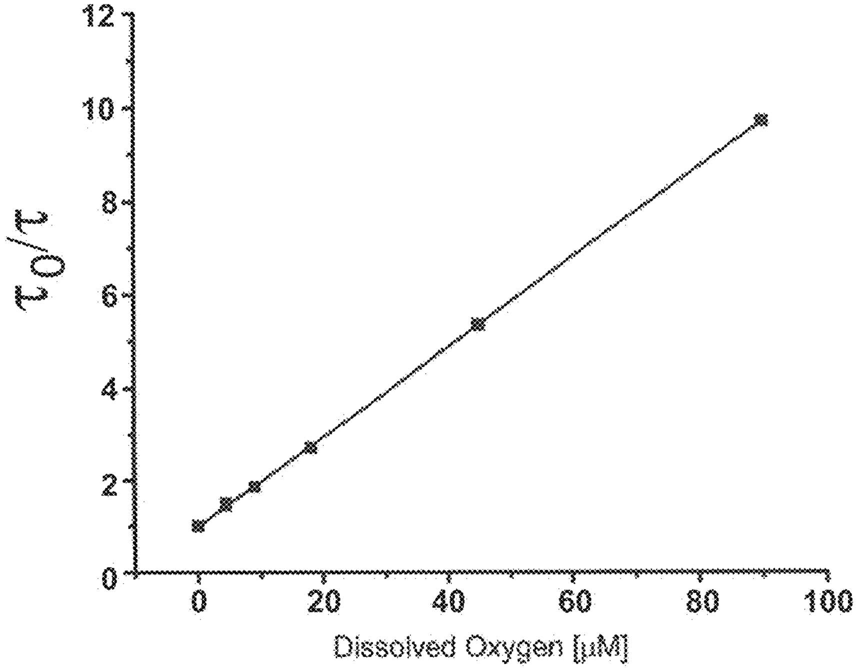
FIG. 10D is a Stern-Volmer plot in 37° C. PBS of PdBMAP-containing 90:10 P(CL-co-DO) (mass ratio of PdBMAP to P(CL-co-DO) is 1:247.8) that was fabricated as described in Example 6.
Figure 11A:
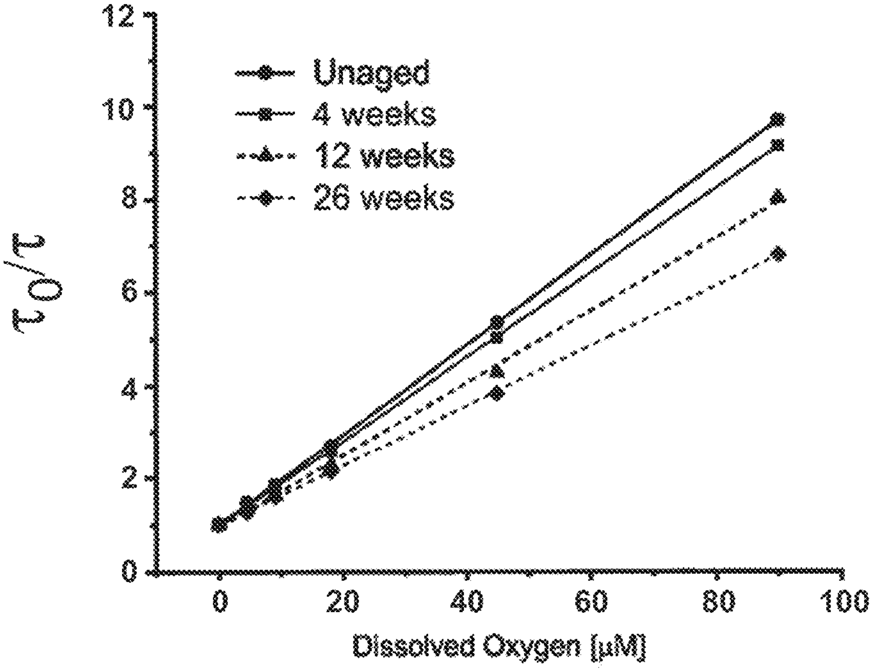
FIG. 11A is the sensor performance as a function of degradation time in 37° C. PBS of PdBMAP-containing 90:10 P(CL-co-DO) (mass ratio of PdBMAP to P(CL-co-DO) is 1:247.8) that was fabricated as described in Example 6.
Figure 11B:
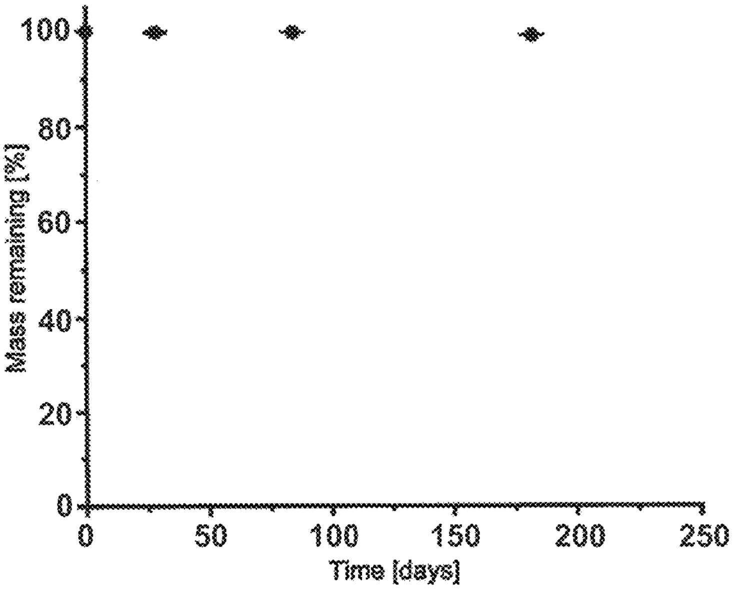
FIG. 11B is the mass loss as a function of degradation time in 37° C. PBS of PdBMAP-containing 90:10 P(CL-co-DO) (mass ratio of PdBMAP to P(CL-co-DO) is 1:247.8) that was fabricated as described in Example 6.
Figure 11C:
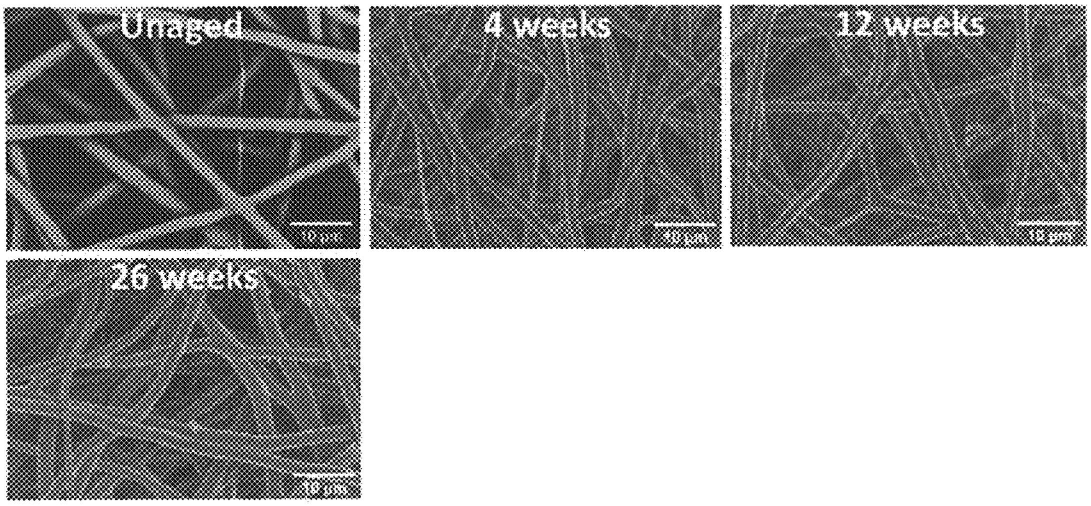
FIG. 11C is the morphology as a function of degradation time in 37° C. PBS of PdBMAP-containing 90:10 P(CL-co-DO) (mass ratio of PdBMAP to P(CL-co-DO) is 1:247.8) that was fabricated as described in Example 6 (scale bar: 10 μm).

Example 6. Process of making and testing a sensor comprising a chromophore and a polymer matrix. Another example of this invention was electrospun 90:10 P(CL-co-DO) that contained PdBMAP at a mass ratio of PdBMAP to P(CL-co-DO) of 1:247.8 that was fabricated under different conditions than the composition of Example 5. The P(CL-co-DO) with 10 mol % of p-dioxanone used in this example had a $M_W$ of 202,700 Da and a melting point of 41° C. To electrospin this composition using a Fluidnatek LE-series machine, the polymer and chromophore were dissolved into 3:1 wt:wt HFIP:DCM such that were was 6 wt % 90:10 P(CL-co-DO) relative to the solvent. The solution was pushed through a 20-gauge needle at a flowrate of 5.0 mL/hr. Applied voltages were +10.0 kV to the needle tip and −1.0 kV to a cylindrical collector rotated at a linear velocity of ~105 cm/s. There was an emitter/collector distance of 20 cm. Temperature was controlled to remain at 25° C., while relative humidity was controlled to be 40%. The speed of translation for the needle along the width of the collector was 10 mm/s. The electrospun scaffold was placed under vacuum for 24 hours to remove residual solvent. The morphology is shown in FIG. 10A, and the average fiber diameter and pore length were ~2.2 and ~29 μm, respectively. After characterization in 37° C. PBS, the composition was observed to exhibit an emission maximum of ~810 nm (FIG. 10B), a red-most absorption maxima of ~630 nm, a to of 135 is, a $K_{SV}$ of $9.7\times10^4$ $M^{-1}$, a $k_q$ of $7.1\times10^8$ $M^{-1}s^{-1}$, and a $1/K_{SV}$ of 10 μM dissolved oxygen. Decay curves were observed to be monoexponential (FIG. 10C), while the Stern-Volmer plot was linear (FIG. 10D). Overall, properties were similar to those observed for 95:5 P(CL-co-DO)+PdBMAP (mass ratio of PdBMAP to P(CL-co-DO) of 1:247.8). The higher PDO content of this 90:10 P(CL-co- DO) composition should result in a shorter degradation time compared to 95:5 P(CL-co-DO). In vitro degradation experiments were conducted for 26 weeks in 37° C. PBS. Oxygen sensor functionality was retained for 26 weeks (FIG. 11A). Although the Stern-Volmer plot remained linear, sensitivity may decrease as a function of aging time. Mass loss (FIG. 11B) and morphological changes (FIG. 11C) observed over this time period were minor. However, after 26 weeks, the sample appeared fragile and would easily tear or fragment if not handle in a sufficiently gentle manner.

Figure 12:
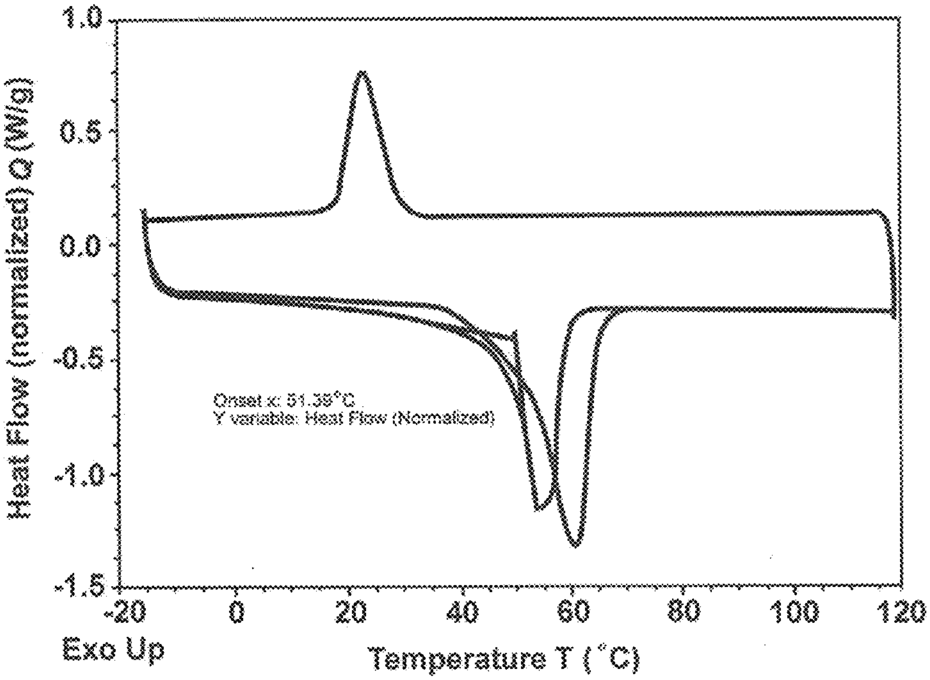
FIG. 12 is the differential scanning calorimetry curves of the poly(ε-caprolactone) (PCL) homopolymer.
Figure 13A:
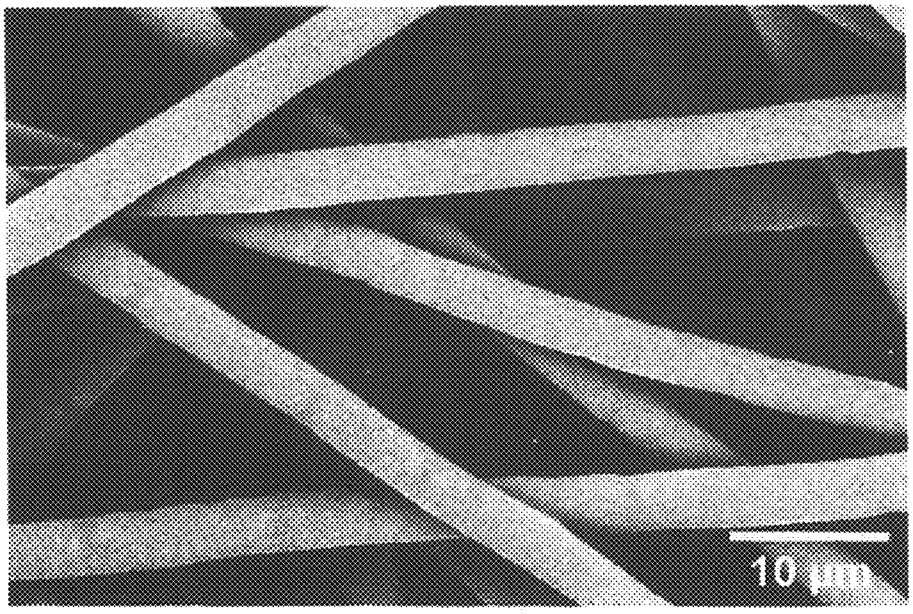
FIG. 13A is the morphology of PdBMAP-containing PCL (mass ratio of PdBMAP to PCL is 1:743.5; scale bar: 10 μm).
Figure 13B:
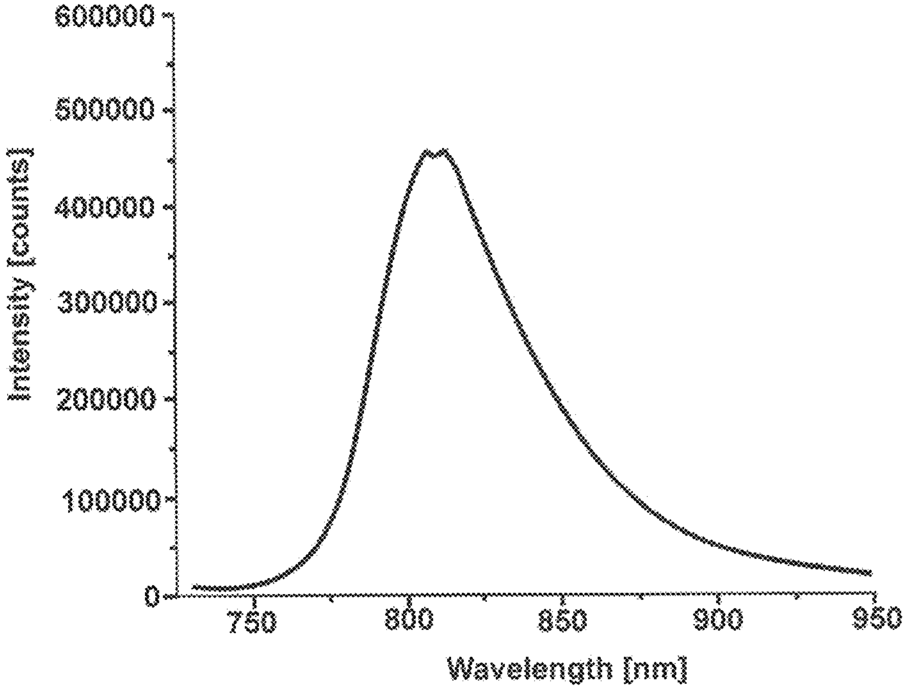
FIG. 13B is an emission spectrum of PdBMAP-containing PCL (mass ratio of PdBMAP to PCL is 1:743.5) in aerated PBS at 37° C.
Figure 13C:
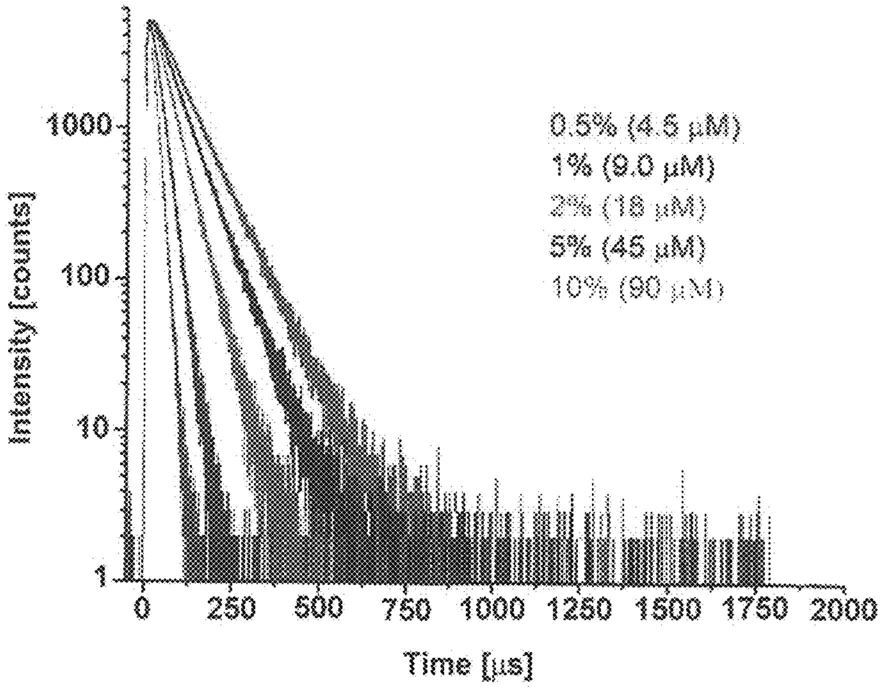
FIG. 13C is phosphorescence decay curves of PdBMAP-containing PCL (mass ratio of PdBMAP to PCL is 1:743.5) at various dissolved oxygen concentrations in 37° C. PBS.
Figure 13D:
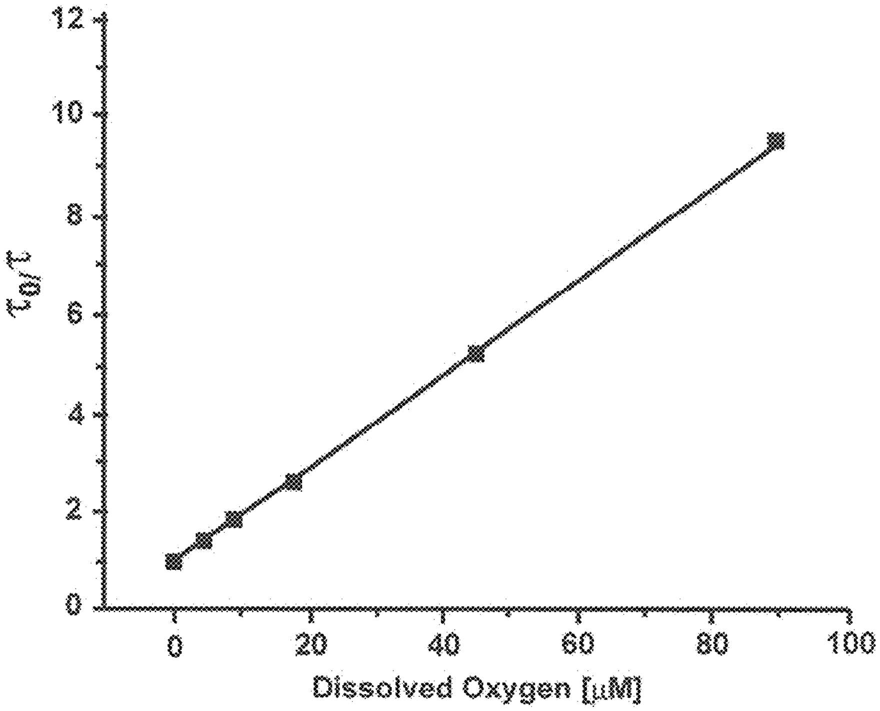
FIG. 13D is a Stern-Volmer plot of PdBMAP-containing PCL (mass ratio of PdBMAP to PCL is 1:743.5) in 37° C. PBS.
Figure 14A:
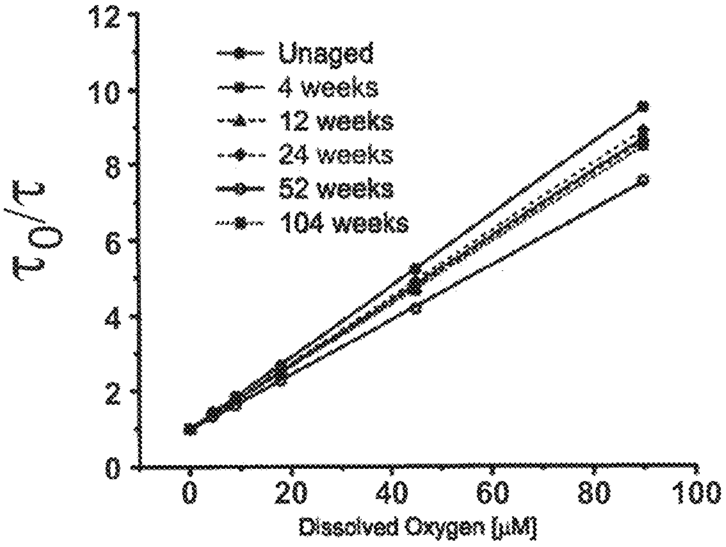
FIG. 14A is the sensor performance of PdBMAP-containing PCL (mass ratio of PdBMAP to PCL is 1:743.5) as a function of degradation time in 37° C. PBS.
Figure 14B:
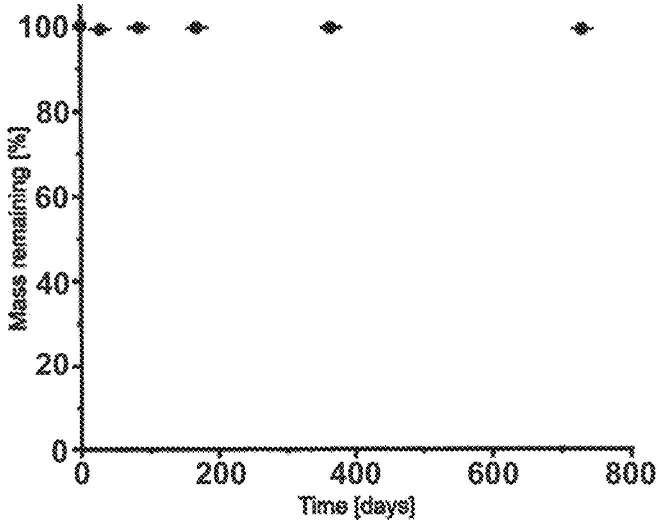
FIG. 14B is the mass loss of PdBMAP-containing PCL (mass ratio of PdBMAP to PCL is 1:743.5) as a function of degradation time in 37° C. PBS.
Figure 14C:
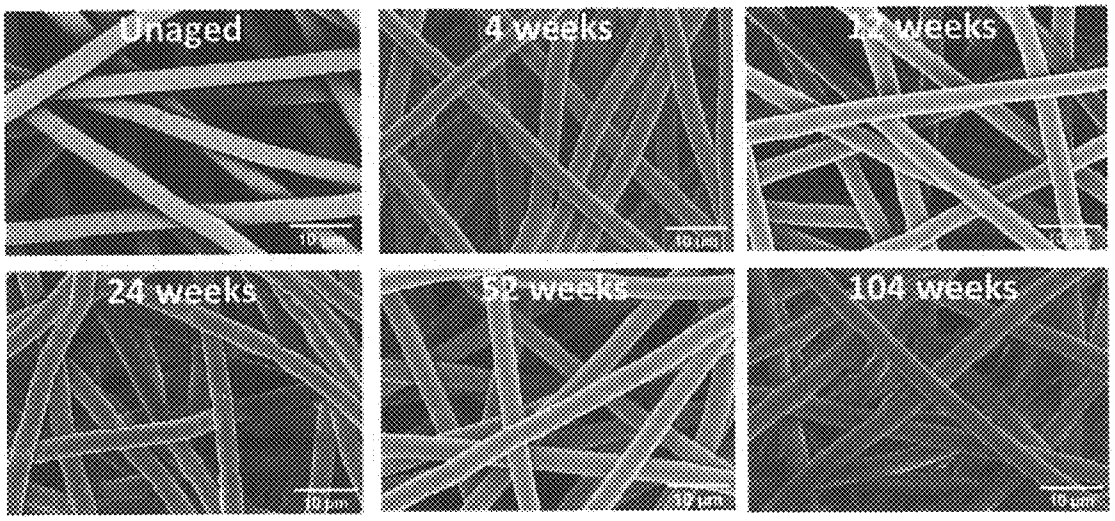
FIG. 14C is the morphology of PdBMAP-containing PCL (mass ratio of PdBMAP to PCL is 1:743.5) as a function of degradation time in 37° C. PBS (scale bar: 10 μm).

Example 7. Process of making and testing a sensor comprising a chromophore and a polymer matrix. An instance of this invention was electrospun poly(ε-caprolactone) that contained PdBMAP at a mass ratio of PdBMAP to PCL of 1:743.5. PCL was obtained from Sigma-Aldrich (Product #440744) and was determined to have a melting point of 51° C. (FIG. 12) and a $M_W$ of 187,200 Da. The electrospinning solution was created by dissolving the polymer and chromophore into HFIP to obtain 10 wt % PCL in HFIP. The composition was electrospun with a Fluidnatek LE-series machine using a 20 gauge needle and a flow rate of 2.0 mL/hr. Voltages of +10 and −0.5 kV were applied to the needle and collector, respectively. The cylindrical collector was 18 cm away from the needle and was rotated such that the linear velocity was ~262 cm/s. The needle translated along the collector width at a translation speed of 10 mm/s. The environmental conditions were set at 25° C. with a relative humidity of 40%. The fabricated samples were exposed to a vacuum for 24 hr to facilitate the removal of residual solvent. The resultant fiber morphology is shown in FIG. 13A; the average fiber diameter and pore length were ~3.7 and ~25 μm, respectively. The composition exhibited an emission maximum of ~810 nm (FIG. 13B) and a red-most absorption maxima of ~630 nm in 37° C. PBS. As characterized in 37° C. PBS, the sensor exhibited a $\tau_0$ of 117 μs, a $K_{SV}$ of $9.5\times10^4$ $M^{-1}$, a $k_q$ of $8.1\times10^8$ $M^{-1}s^{-1}$, and a $1/K_{SV}$ of 11 μM dissolved oxygen. Phosphorescence decays were monoexponential (FIG. 13C), and the Stem-Volmer plot was linear (FIG. 13D). These attributes indicate a homogenous chromophore environment. Since the $1/K_{SV}$ of 11 μM is below expected healthy physiological levels, this composition appears to be well suited for monitoring hypoxia. PCL is bioresorbable but is expected to take approximately 2-3 years to fully degrade in vivo. In vitro degradation experiments were conducted, and oxygen sensor functionality was retained for 104 weeks (FIG. 14A). Mass loss (FIG. 14B) and morphological changes (FIG. 14C) were negligible over this time period.

Figure 15A:
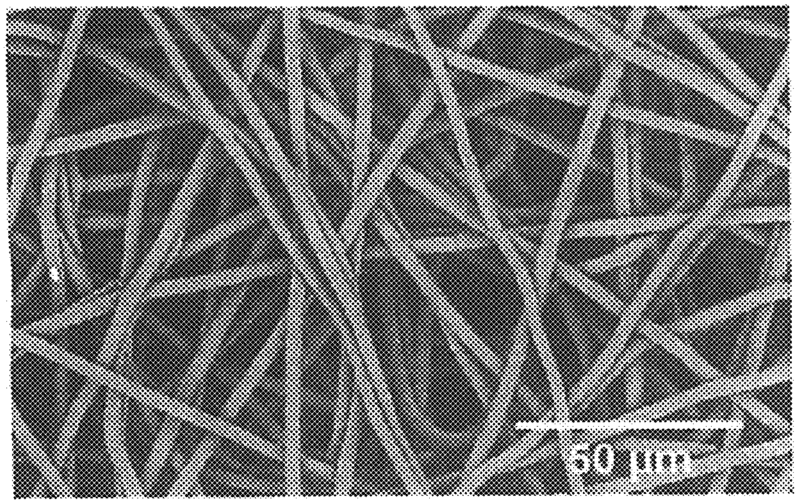
FIG. 15A is the morphology of PdBMAP-containing PCL (mass ratio of PdBMAP to PCL is 1:176.7; scale bar: 50 μm).
Figure 15B:
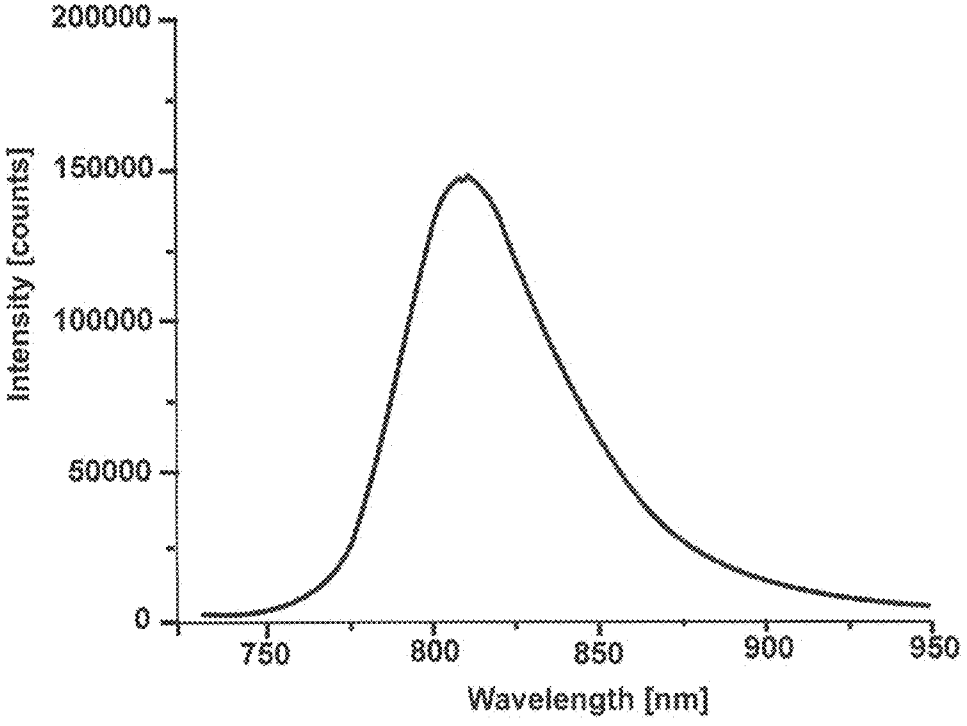
FIG. 15B is an emission spectrum of PdBMAP-containing PCL (mass ratio of PdBMAP to PCL is 1:176.7) in aerated PBS at 37° C.
Figure 15C:
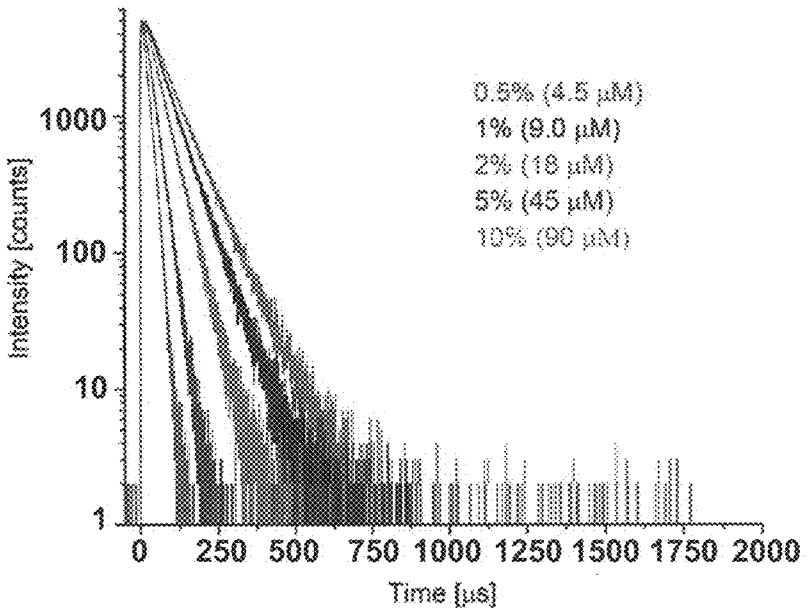
FIG. 15C is phosphorescence decay curves of PdBMAP-containing PCL (mass ratio of PdBMAP to PCL is 1:176.7) at various dissolved oxygen concentrations in 37° C. PBS.
Figure 15D:
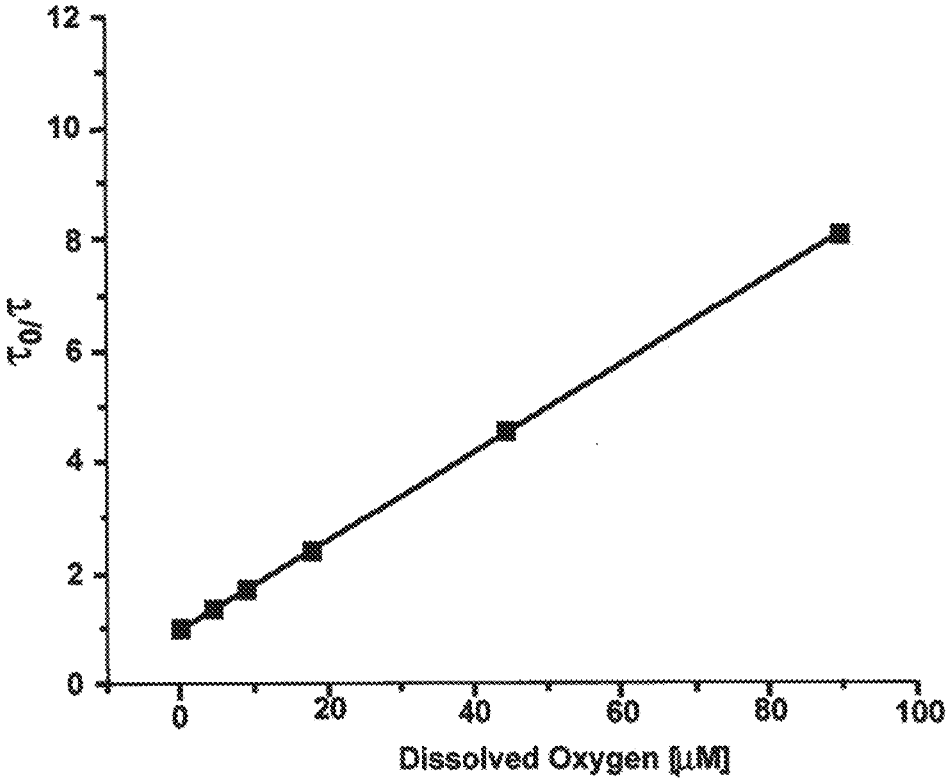
FIG. 15D is a Stem-Volmer plot of PdBMAP-containing PCL (mass ratio of PdBMAP to PCL is 1:176.7) in 37° C. PBS.
Figure 16:
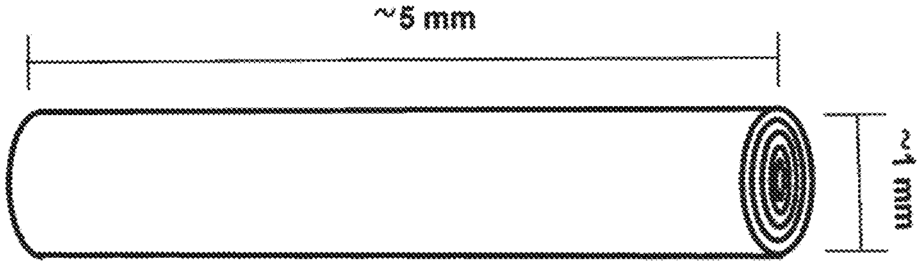
FIG. 16 is a schematic of the electrospun scaffold rolled into a cylinder.

Example 8. Process of making and testing a sensor comprising a chromophore and a polymer matrix. Another example of this invention is PCL+PdBMAP for which PdBMAP is present at a mass ratio of PdBMAP to PCL of 1:176.7. Except for the increased chromophore concentration, this example was fabricated as previously described for Example 7. The electrospun morphology is shown in FIG. 15A; the average fiber diameter and pore length were ~3.6 and ~23 μm, respectively. As characterized in 37° C. PBS, the composition exhibited an emission maximum of ~810 nm (FIG. 15B), a red-most absorption maxima of ~630 nm, a $\tau_0$ of 98 μs, a $K_{SV}$ of $7.9\times10^4$ $M^{-1}$, a $k_q$ of $8.0\times10^8$ and a $1/K_{SV}$ of 13 μM dissolved oxygen. Phosphorescence decays were monoexponential (FIG. 15C), and the Stern-Volmer plot was linear (FIG. 15D). These observations indicate that the oxygen sensing properties remained similar to the composition described in Example 7 (mass ratio of PdBMAP to PCL of 1:743.5) and that the chromophore environment remained homogenous when the mass ratio of PdBMAP to PCL was 1:176.7. This indicates the potential to increase chromophore concentration as high as a mass ratio of PdBMAP to PCL of 1:176.7 in order to enhance emission intensity.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A bioresorbable sensor implantable into an animal or human for optical detection of tissue oxygenation, said sensor comprising a chromophore and a polymer matrix, said chromophore being uniformly dispersed within said polymer matrix, said sensor having a pore length of at least 20 μm, said chromophore being present in mass ratio of chromophore to polymer of from about 1:2000 to about 1:100, said chromophore when in said polymer matrix exhibiting a red-most absorption maxima and emission maximum of from about 600 nm to about 1300 nm, said chromophore when in said polymer matrix having a difference between the red-most absorption maxima and the emission maximum that is greater than or equal to 50 nm, and said polymer matrix comprising one or more biocompatible and bioresorbable synthetic copolymers and/or homopolymers; said copolymers having each independently a weight-average molecular weight of at least 75,000 Da, said homopolymers having each independently a weight-average molecular weight of at least 75,000 Da and/or said homopolymers having each independently an inherent viscosity of at least 1.0 dL/g.

2. The sensor of claim 1, said sensor comprising a chromophore and a polymer matrix, said chromophore being uniformly dispersed within said polymer matrix, said sensor has a pore length of from about 20 μm to about 50 μm, said chromophore being present in mass ratio of chromophore to polymer of from about 1:1000 to about 1:100, said chromophore when in said polymer matrix having a deaerated phosphorescence lifetime in 37° C. phosphate-buffered saline of at least 50 μs, said chromophore when in said polymer matrix exhibiting a red-most absorption maxima and emission maximum of from about 600 nm to about 1000 nm, said chromophore when in said polymer matrix having a difference between the red-most absorption maxima and the emission maximum that is from about 100 nm to about 300 nm, said chromophore being selected from the group consisting of Pd (II) and Pt (II) benzoporphyrins and mixtures thereof, and said polymer matrix comprising one or more copolymers and/or homopolymers, said one or more copolymers being selected from the group consisting of biocompatible and bioresorbable polyesters, said copolymers each independently having a weight-average molecular weight of from about 75,000 Da to about 350,000 Da, said one or more homopolymers being selected from the group consisting of biocompatible and bioresorbable polyesters, said homopolymers having each independently a weight-average molecular weight of from about 75,000 Da to about 350,000 Da, and/or said homopolymers having each independently an inherent viscosity of from about 1.0 dL/g to about 3.0 dL/g.

3. The sensor of claim 1, said sensor comprising a chromophore and a polymer matrix, said chromophore being uniformly dispersed within said polymer matrix, said sensor having a pore length of from about 20 μm to about 40 μm, said chromophore being present in mass ratio of chromophore to polymer of from about 1:1000 to about 1:125, said chromophore when in said polymer matrix having a deaerated phosphorescence lifetime in 37° C. phosphate-buffered saline of from about 90 μs to about 500 μs, said chromophore when in said polymer matrix exhibiting a red-most absorption maxima and emission maximum of from about 600 nm to about 1000 nm, said chromophore when in said polymer matrix having a difference between the red-most absorption maxima and the emission maximum that is from about 100 nm to about 300 nm, said chromophore being selected from the group consisting of Pd (II) tetramethacrylated benzoporphyrin, Pt (II) tetramethacrylated benzoporphyrin, Pd (II) meso-tetraphenyl tetrabenzoporphyrin, or Pt (II) meso-tetraphenyl tetrabenzoporphyrin, more preferably said chromophore is Pd (II) tetramethacrylated benzoporphyrin and said polymer matrix comprises poly(ε-caprolactone-co-p-dioxanone) and/or homopolymers selected from the group consisting of poly(p-dioxanone), poly(ε-caprolactone), and mixtures thereof; said copolymers having each independently a weight-average molecular weight of from about 115,000 Da to about 350,000 D; said homopolymers having each independently a weight-average molecular weight of from about 115,000 Da to about 350,000 Da and/or said homopolymers each independently having an inherent viscosity of from about 1.5 dL/g to about 3.0 dL/g.

4. The sensor of claim 1, said sensor having a fiber diameter of at least 1 μm.

5. The sensor of claim 1, said sensor having a fiber diameter of from about 1 μm to about 7.

6. The sensor of claim 1, said sensor having a fiber diameter of from about 1 μm to about 5 μm.

7. The sensor of claim 1 said sensor having a melting point of about 38° C. or higher.

8. The sensor of claim 1, said sensor having a rolled cylindrical or rectangular prism geometry.

9. The sensor of claim 1, said sensor having:

a.) a Stern-Volmer quenching constant of from about $1.11\times10^4$ $M^{-1}$ to about $1.00\times10^6$ $M^{-1}$; and/or b.) a dissolved oxygen concentration at which the phosphorescence lifetime of the sensor is quenched to 50% of its deaerated phosphorescence lifetime of from about 1 μM to about 90 μM.

10. The sensor of claim 1, said sensor having:

a.) a Stern-Volmer quenching constant of from about $1.11\times10^4$ $M^{-1}$ to about $2.00\times10^5$ $M^{-1}$; and/or b.) a dissolved oxygen concentration at which the phosphorescence lifetime of the sensor is quenched to 50% of its deaerated phosphorescence lifetime of from about 5 μM to about 90 μM.

11. The sensor of claim 1, said sensor having:

a.) a Stern-Volmer quenching constant of from about $1.43\times10^4$ $M^{-1}$ to about $2.00\times10^5$ $M^{-1}$; and/or b.) a dissolved oxygen concentration at which the phosphorescence lifetime of the sensor is quenched to 50% of its deaerated phosphorescence lifetime of from about 5 μM to about 70 μM.

12. The sensor of claim 1, said sensor having:

a.) a Stern-Volmer quenching constant of from about $2.22\times10^4$ $M^{-1}$ to about $1.43\times10^5$ $M^{-1}$; and/or b.) a dissolved oxygen concentration at which the phosphorescence lifetime of the sensor is quenched to 50% of its deaerated phosphorescence lifetime of from about 7 μM to about 45 μM.

13. A sensor system comprising a sensor and a patch reader, said patch reader comprising one or more light-emitting diodes having a peak wavelength that at least in part overlaps with a red-most absorption peak of a sensor composition, and said sensor comprising a chromophore and a polymer matrix, said chromophore being uniformly dispersed within said polymer matrix, said sensor having a pore length of at least 20 μm, said chromophore being present in mass ratio of chromophore to polymer of from about 1:2000 to about 1:100, said chromophore when in said polymer matrix exhibiting a red-most absorption maxima and emission maximum of from about 600 nm to about 1300 nm, said chromophore when in said polymer matrix having a difference between the red-most absorption maxima and the emission maximum that is greater than or equal to 50 nm, and said polymer matrix comprising one or more copolymers and/or homopolymers; said copolymers having each independently a weight-average molecular weight of at least 75,000 Da, said homopolymers having each independently a weight-average molecular weight of at least 75,000 Da and/or said homopolymers having each independently an inherent viscosity of at least 1.0 dL/g.

14. The sensor system of claim 13, said sensor system comprising a sensor according to claim 1 and a patch reader, said patch reader being a wired or an unwired patch reader that contains a photodetector capable of recording phosphorescence decays of the sensor composition in terms of voltage versus time, said patch reader comprises one or more light-emitting diodes having a peak wavelength that at least in part overlaps with a red-most absorption peak of a sensor composition, said light-emitting diodes being intensity-adjustable and having a peak wavelength of from about 600 nm to about 700 nm.

15. The sensor system of claim 13, said sensor system comprising a sensor according to claim 1 and a patch reader, said patch reader being a wired or an unwired patch reader that contains a photodetector capable of recording phosphorescence decays of the sensor composition in terms of voltage versus time, said photodetector having a resolution of at least 5 μs, said patch reader comprising a stray excitation light blocking filter covering the photodetector, said patch reader comprising four or more said light-emitting diodes that surround said photodetector, said light-emitting diodes having a peak wavelength that at least in part overlaps with a red-most absorption peak of a sensor composition, said light-emitting diodes being intensity-adjustable and having a peak wavelength of from about 600 nm to about 700 nm.

16. The sensor system of claim 15, wherein said patch reader comprises a temperature sensor that records temperature versus time.

17. A process of making a sensor, said process comprising the steps of:

a.) electrospinning a solution comprising a solvent, polymer and chromophore to form a sensor scaffold; said solution, comprising, based on total solution weight, of from about 3% to about 20% polymer, said chromophore being present in mass ratio of chromophore to polymer of from about 1:2000 to about 1:100, and said solvent being selected from the group of 1,1,1,3,3,3-hexafluoro-2-propanol, dichloromethane, and mixtures thereof; said electrospinning process having one or more syringes containing said solution, each said syringe being attached to an electrospinning needle, each electrospinning needle independently having an electrospinning needle gauge of from about 14 gauge to 24 gauge, each said needle being translated or being stationary, each electrospinning needle independently having a flow rate of solution comprising a polymer and chromophore of from about 0.5 mL/hr to about 15 mL/hr, each electrospinning needle independently having a voltage applied to said electrospinning needle of from about +5 kV to about +28 kV, and one or more electrospinning collectors, each said electrospinning collector having a voltage applied to each said electrospinning collector of from about −0.2 kV to about −10 kV, each said electrospinning collector independently having an electrospinning collector motion linear velocity of from about 50 cm/s to about 600 cm/s, said process having a distance between electrospinning needle(s) and electrospinning collector(s) of from 12 cm to about 30 cm, said process having a controlled electrospinning exposure temperature of from about 20° C. to about 40° C., and said process having a controlled electrospinning exposure relative humidity of from about 0% relative humidity to about 50% relative humidity; and b.) processing said sensor scaffold into a sensor by a process comprising rolling and/or cutting said scaffold.

18. The process of making a sensor according to claim 17, said process comprising the steps of:

a) electrospinning a solution comprising a solvent, polymer and chromophore to form a sensor scaffold; said solution, comprising, based on total solution weight, of from about 3% to about 15% polymer, said chromophore being present in mass ratio of chromophore to polymer of from about 1:1000 to about 1:100, and said solvent being selected from the group of 1,1,1,3,3,3-hexafluoro-2-propanol, dichloromethane, and mixtures thereof; said electrospinning process having one or more syringes containing said solution, each said syringe being attached to an electrospinning needle, each electrospinning needle independently having an electrospinning needle gauge of from about 16 gauge to about 24 gauge, each said needle being translated and each electrospinning needle independently having an electrospinning needle translation speed of from about 1 mm/s to about 50 mm/s, each electrospinning needle independently having a flow rate of solution comprising a polymer and chromophore of from about 1 mL/hr to about 8 mL/hr, each electrospinning needle independently having a voltage applied to each said electrospinning needle of about +6 kV to about +15 kV, and one or more electrospinning collectors, each said electrospinning collector independently having a voltage applied to each said electrospinning collector of from about −0.2 kV to about −6.0 kV, each said electrospinning collector independently having an electrospinning collector motion linear velocity from about 100 cm/s to about 500 cm/s, said process having a distance between electrospinning needle(s) and electrospinning collector(s) of from about 14 cm to about 22 cm, said process having a controlled electrospinning exposure temperature of from about 20° C. to about 30° C., and said process having a controlled electrospinning exposure relative humidity of about 20% relative humidity to about 50% relative humidity; and b) processing said sensor scaffold into a sensor by a process comprising rolling and/or cutting said scaffold.

19. The process of making a sensor according to claim 17, said process comprising the steps of:

a) electrospinning a solution comprising a solvent, polymer and chromophore to form a sensor scaffold; said solution, comprising, based on total solution weight, of from about 5% to about 15% polymer, said chromophore being present in mass ratio of chromophore to polymer of from about 1:1000 to about 1:125, and said solvent being selected from the group of 1,1,1,3,3,3-hexafluoro-2-propanol, dichloromethane, and mixtures thereof; said electrospinning process having one or more syringes containing said solution, each said syringe being attached to an electrospinning needle, each electrospinning needle independently having an electrospinning needle gauge of from about 18 gauge to about 22 gauge, each said needle being translated and each electrospinning needle independently having an electrospinning needle translation speed of from about 5 mm/s to about 30 mm/s, each electrospinning needle independently having a flow rate of solution comprising a polymer and chromophore from about 1 mL/hr to about 6 mL/hr, each electrospinning needle independently having a voltage applied to each said electrospinning needle of from about +8 kV to about +12 kV, and one or more electrospinning collectors, each said electrospinning collector having a voltage applied to said electrospinning collector of from about −0.2 kV to about −4.0 kV, each said electrospinning collector independently having an electrospinning collector motion linear velocity of from about 100 cm/s to about 300 cm/s, said process having a distance between electrospinning needle(s) and electrospinning collector(s) of from about 18 cm to about 22 cm, said process having a controlled electrospinning exposure temperature of from about 22° C. to about 26° C., and said process having a controlled electrospinning exposure relative humidity of from about 35% relative humidity to about 45% relative humidity; and b) processing said sensor scaffold into a sensor by a process comprising rolling and/or cutting said scaffold.

20. A method of determining tissue oxygenation comprising:

a.) stimulating a sensor that is implanted in an animal or human with light having a peak wavelength of from about 600 nm to about 700 nm to cause the emission of light, said light having an emission maximum wavelength of from about 750 nm to about 900 nm, wherein said sensor comprises a chromophore and a polymer matrix, said chromophore being uniformly dispersed within said polymer matrix, said sensor having a pore length of at least 20 μm, said chromophore being present in mass ratio of chromophore to polymer of from about 1:2000 to about 1:100, said chromophore when in said polymer matrix exhibiting a red-most absorption maxima and emission maximum of from about 600 nm to about 1300 nm, said chromophore when in said polymer matrix having a difference between the red-most absorption maxima and the emission maximum that is greater than or equal to 50 nm, and said polymer matrix comprising one or more copolymers and/or homopolymers; said copolymers having each independently a weight-average molecular weight of at least 75,000 Da, said homopolymers having each independently a weight-average molecular weight of at least 75,000 Da and/or said homopolymers having each independently an inherent viscosity of at least 1.0 dL/g;

b.) fitting the intensity of the emitted light versus time with an exponential function;

c.) obtaining a phosphorescence lifetime from said fit; and d.) optionally monitoring said phosphorescence lifetime versus time and/or comparing said phosphorescence lifetime to a calibration.

21. The method of determining tissue oxygenation according to claim 20, said method comprising:

a) stimulating a sensor according to claim 1 that is implanted in an animal or human with light having a peak wavelength of from about 600 nm to about 700 nm to cause the emission of light, said light having an emission maximum wavelength of from about 750 nm to about 900 nm;

b) fitting the intensity of the emitted light versus time with an exponential function, said exponential function is selected from a monoexponential decay function $I=I_{bkgd}+A\exp(-t/\tau)$, where I is a signal intensity of a chromophore, $I_{bkgd}$ is a background signal intensity of an environment of said chromophore, A is the pre-exponential factor of said monoexponential decay function, t is a time elapsed during a lifetime measurement, and $\tau$ is the phosphorescence lifetime of said chromophore; or a biexponential decay function $I=I_{bkgd}+A_1\exp(-t/\tau_1)+A_2\exp(-t/\tau_2)$, where I is the signal intensity of a chromophore, $I_{bkgd}$ is the background signal intensity of an environment of said chromophore, tis time elapsed during a lifetime measurement, $A_1$ is a first pre-exponential factor of said biexponential decay function, $\tau_1$ is a first phosphorescence lifetime of said chromophore, $A_2$ is a second pre-exponential factor of said biexponential decay function, and $\tau_2$ is a second phosphorescence lifetime of said chromophore;

c) obtaining a phosphorescence lifetime from said fit; using a biexponential decay function, wherein the obtained lifetime is the amplitude average phosphorescence lifetime ($\tau_m=(A_1\tau_1+A_2\tau_2)/(A_1+A_2)$), where $\tau_m$ is the amplitude average phosphorescence lifetime of said chromophore, $A_1$ is a first pre-exponential factor of said biexponential decay function, $\tau_1$ is a first phosphorescence lifetime of said chromophore, $A_2$ is a second pre-exponential factor of said biexponential decay function, and $\tau_2$ is a second phosphorescence lifetime of said chromophore;

d) optionally monitoring said phosphorescence lifetime versus time and/or comparing said phosphorescence lifetime to a calibration, said calibration being performed using the Stern-Volmer equation ($\tau_0/\tau=1+K_{SV}[O_2]$), where $\tau_0$ is the deaerated phosphorescence lifetime of said chromophore, $\tau$ is the phosphorescence lifetime of said chromophore at a dissolved oxygen concentration, $[O_2]$ is a dissolved oxygen concentration, and $K_{SV}$ is the Stern-Volmer quenching constant and to and $K_{SV}$ are obtained from the in vitro characterization of the composition in 37° C. phosphate-buffered saline as described according to this specification's Test Method 1.

22. The method of claim 20 comprising monitoring said phosphorescence lifetime versus time and/or comparing said phosphorescence lifetime to a calibration.

23. The method of claim 20 comprising monitoring said phosphorescence lifetime versus time and/or comparing said phosphorescence lifetime to a calibration, wherein said calibration is performed using the Stern-Volmer equation ($\tau_0/\tau=1+K_{SV}[O_2]$), where $\tau_0$ is the deaerated phosphorescence lifetime of said chromophore, $\tau$ is the phosphorescence lifetime of said chromophore at a dissolved oxygen concentration, $[O_2]$ is a dissolved oxygen concentration, and $K_{SV}$ is the Stern-Volmer quenching constant and to and $K_{SV}$ are obtained from the in vitro characterization of the composition in 37° C. phosphate-buffered saline as described according to this specification's Test Method 1.

24. A sensor comprising a chromophore and a polymer matrix, said chromophore being uniformly dispersed within said polymer matrix, said sensor having a pore length of at least 20 μm, said chromophore being present in mass ratio of chromophore to polymer of from about 1:2000 to about 1:100, said chromophore when in said polymer matrix exhibiting a red-most absorption maxima and emission maximum of from about 600 nm to about 1300 nm, said chromophore when in said polymer matrix having a difference between the red-most absorption maxima and the emission maximum that is greater than or equal to 50 nm, and said polymer matrix comprising one or more copolymers and/or homopolymers; said copolymers having each independently a weight-average molecular weight of at least 75,000 Da, said homopolymers having each independently a weight-average molecular weight of at least 75,000 Da and/or said homopolymers having each independently an inherent viscosity of at least 1.0 dL/g; and wherein said sensor comprises a chromophore and a polymer matrix, said chromophore being uniformly dispersed within said polymer matrix, said sensor has a pore length of from about 20 μm to about 50 μm, said chromophore being present in mass ratio of chromophore to polymer of from about 1:1000 to about 1:100, said chromophore when in said polymer matrix having a deaerated phosphorescence lifetime in 37° C. phosphate-buffered saline of at least 50 μs, said chromophore when in said polymer matrix exhibiting a red-most absorption maxima and emission maximum of from about 600 nm to about 1000 nm, said chromophore when in said polymer matrix having a difference between the red-most absorption maxima and the emission maximum that is from about 100 nm to about 300 nm, said chromophore being selected from the group consisting of Pd (II) and Pt (II) benzoporphyrins and mixtures thereof, and said polymer matrix comprising one or more copolymers and/or homopolymers, said one or more copolymers being selected from the group consisting of biocompatible and bioresorbable polyesters, said copolymers each independently having a weight-average molecular weight of from about 75,000 Da to about 350,000 Da, said one or more homopolymers being selected from the group consisting of biocompatible and bioresorbable polyesters, said homopolymers having each independently a weight-average molecular weight of from about 75,000 Da to about 350,000 Da, and/or said homopolymers having each independently an inherent viscosity of from about 1.0 dL/g to about 3.0 dL/g.

25. A sensor comprising a chromophore and a polymer matrix, said chromophore being uniformly dispersed within said polymer matrix, said sensor having a pore length of at least 20 μm, said chromophore being present in mass ratio of chromophore to polymer of from about 1:2000 to about 1:100, said chromophore when in said polymer matrix exhibiting a red-most absorption maxima and emission maximum of from about 600 nm to about 1300 nm, said chromophore when in said polymer matrix having a difference between the red-most absorption maxima and the emission maximum that is greater than or equal to 50 nm, and said polymer matrix comprising one or more copolymers and/or homopolymers; said copolymers having each independently a weight-average molecular weight of at least 75,000 Da, said homopolymers having each independently a weight-average molecular weight of at least 75,000 Da and/or said homopolymers having each independently an inherent viscosity of at least 1.0 dL/g; and wherein said sensor comprising a chromophore and a polymer matrix, said chromophore being uniformly dispersed within said polymer matrix, said sensor having a pore length of from about 20 μm to about 40 μm, said chromophore being present in mass ratio of chromophore to polymer of from about 1:1000 to about 1:125, said chromophore when in said polymer matrix having a deaerated phosphorescence lifetime in 37° C. phosphate-buffered saline of from about 90 μs to about 500 μs, said chromophore when in said polymer matrix exhibiting a red-most absorption maxima and emission maximum of from about 600 nm to about 1000 nm, said chromophore when in said polymer matrix having a difference between the red-most absorption maxima and the emission maximum that is from about 100 nm to about 300 nm, said chromophore being selected from the group consisting of Pd (II) tetramethacrylated benzoporphyrin, Pt (II) tetramethacrylated benzoporphyrin, Pd (II) meso-tetraphenyl tetrabenzoporphyrin, or Pt (II) meso-tetraphenyl tetrabenzoporphyrin, more preferably said chromophore is Pd (II) tetramethacrylated benzoporphyrin and said polymer matrix comprises poly(ε-caprolactone-co-p-dioxanone) and/or homopolymers selected from the group consisting of poly(p-dioxanone), poly(ε-caprolactone), and mixtures thereof; said copolymers having each independently a weight-average molecular weight of from about 115,000 Da to about 350,000 D; said homopolymers having each independently a weight-average molecular weight of from about 115,000 Da to about 350,000 Da and/or said homopolymers each independently having an inherent viscosity of from about 1.5 dL/g to about 3.0 dL/g.

* * * * *